United States Patent
Svarovsky et al.

(10) Patent No.: US 11,542,226 B2
(45) Date of Patent: Jan. 3, 2023

(54) POLYFUNCTIONAL CANNABINOIDS

(71) Applicant: Axim Biotechnologies, Inc., New York, NY (US)

(72) Inventors: Sergei Svarovsky, San Diego, CA (US); John W. Huemoeller, II, Golden, CO (US)

(73) Assignee: Axim Biotechnologies, Inc., New York, NY (US)

( * ) Notice: Subject to any disclaimer, the term of this patent is extended or adjusted under 35 U.S.C. 154(b) by 0 days.

(21) Appl. No.: 17/229,041

(22) Filed: Apr. 13, 2021

(65) Prior Publication Data

US 2021/0332004 A1    Oct. 28, 2021

Related U.S. Application Data

(60) Provisional application No. 63/014,471, filed on Apr. 23, 2020.

(51) Int. Cl.
*C07C 235/48* (2006.01)
*C07D 311/80* (2006.01)

(52) U.S. Cl.
CPC .......... *C07C 235/48* (2013.01); *C07D 311/80* (2013.01)

(58) Field of Classification Search
CPC .................................................. C07C 235/48
See application file for complete search history.

(56) References Cited

U.S. PATENT DOCUMENTS 6,509,005 B1 * 1/2003 Peart .................. A61P 1/14
424/45

FOREIGN PATENT DOCUMENTS

WO    WO-2007056242 A1 * 5/2007 ........... A61K 31/352

* cited by examiner

*Primary Examiner* — Golam M Shameem
(74) *Attorney, Agent, or Firm* — Premium IP Services, P.C.

(57) ABSTRACT

This invention discloses cannabinoids linked with polyethylene glycol chains. The cannabinoid-polyethylene glycol chain molecules have one, two, or more cannabinoids linked with one, two, or more polyethylene glycol chains. Each cannabinoid-polyethylene glycol chain molecule may have one kind of cannabinoid or multiple kinds of cannabinoid. Methods to make these cannabinoid-polyethylene glycol linked chains are disclosed.

3 Claims, 2 Drawing Sheets

Mass spectrum of olivetolic acid phenethylamine adduct

NMR spectrum of olivetolic acid phenethylamine adduct

CBDA-PEG7 Mass Spectrum

CBDA-PEG7 NMR Spectrum

POLYFUNCTIONAL CANNABINOIDS

CROSS-REFERENCE TO RELATED APPLICATIONS

This application claims the benefit of U.S. Provisional Application No. 63/014,471, filed Apr. 23, 2020. Each of the above-referenced patent applications is incorporated by reference in its entirety.

BACKGROUND OF THE INVENTION

Field of the Invention

This invention relates to compounds of poly-functional linked cannabinoids, where one or more cannabinoids are chemically linked with a polyethylene glycol (PEG) molecule acting as a linker to increase solubility, improve circulation time, and/or to increase potency of the resulting compound.

The cannabis plant has many naturally occurring substances that are of great interest in the fields of science and medicine. Isolated compounds from the cannabis plant include $\Delta^9$-tetrahydrocannabinol (THC), cannabidiol (CBD), cannabichromene (CBC), cannabigerol (CBG), cannabidivarin (CBDV), cannabinol (CBN), cannabichromene (CBC), cannabivarin (CBV), among other compounds. While THC has psychoactive effects, CBD, CBC, CBG, and CBDV do not. Isolated compounds from the cannabis plant are called cannabinoids. There are a total of one hundred thirteen (113) cannabinoids that have been isolated from the cannabis plant. Many researchers have confirmed the medicinal value of cannabinoids. Cannabinoids have been investigated for possible treatment of seizures, nausea, vomiting, lack of appetite, pain, arthritis, inflammation, and other conditions.

The IUPAC nomenclature of THC is (-)-(6aR,10aR)-6,6,9-trimethyl-3-pentyl-6a,7,8,10a-tetrahydro-6H-benzo[c]chromen-1-ol. CBD's IUPAC nomenclature is 2-((1S,6S)-3-methyl-6-(prop-1-en-2-yl)cyclo-hex-2-enyl)-5-pentylbenzene-1,3-diol). CBC has the IUPAC nomenclature of 2-methyl-2-(4-methylpent-3-enyl)-7pentyl-5-chromenol. CBG's IUPAC nomenclature is 2-[(2E)-3,7-Dimethylocta-2,6-dienyl]-5-pentyl-benzene-1,3-diol. CBDV's has a IUPAC nomenclature of 2-((1S,6S)-3-methyl-6-(prop-1-en-2-yl)cyclohex-2-enyl)-5-propylbenzene-1,3-diol. CBN's IUPAC nomenclature is 6,6, 9-Trimethyl-3-pentyl-benzo[c]chromen-1-ol. CBV's IUPAC nomenclature is 6,6,9-Trimethyl-3-propyl-6H-dibenzo[b,d]pyran-1-ol. These are among the most prominent compounds in the family of compounds extracted from the cannabis plant referred to as cannabinoids.

Natural cannabinoids may be isolated by extraction from cannabis plants. Plants in the cannabis genus include *Cannabis sativa*, *Cannabis ruderalis*, and *Cannabis indica*. These plants are the natural sources of cannabinoids. Cannabinoids are also available in synthetic forms. Methods to synthesize cannabinoids in lab settings were discovered and are still currently practiced. Synthetic cannabinoids are more targeted, in that the synthetic compound usually comes isolated without other cannabinoids mixed in.

Nabilone (racemic(6aR,10aR)-1-hydroxy-6,6-dimethyl-3-(2-methyloctan-2-yl)-7,8,10,10a-tetrahydro-6H-benzo[c]chromen-9(6aH)-one), a synthetic cannabinoid, is believed to have fewer undesired side effects than THC. Nabilone mimics the chemical compound structure of THC. THC also exists in synthetic form under the name Dronabinol ((-)-(6aR,10aR)-6,6,9-trimythel-3-pentyl-6a,7,8,10a-tetrahydro-6H-benzo[c]chromen-1-ol)). These synthetic cannabinoids are investigated for medicinal purposes. The U.S. Food and Drug Administration approved nabilone for treatment of chemotherapy-induced nausea and vomiting. In the United States, nabilone is marketed under the name Cesamet®.

Cannabidiol from hemp is marketed in the United States. Various products containing cannabidiol have been marketed in recent years. Cannabidiol may be consumed by ingestion, by inhalation, or by transdermal delivery.

Conspicuous in the challenges of deploying cannabinoids into various pharmaceutical, supplement, and food products is the lack of solubility. Highly lipophilic, cannabinoids do not fit in well with some products for oral consumption, especially with beverage type of products. Some cannabinoid pharmaceutical products such as Nabilone is best consumed by placing under the tongue to bypass metabolism. Cannabinoids have never been considered to be a candidate for intravenous delivery.

Cannabinoids are highly lipophilic molecules with very low solubility in water (2-10 µg/mL). Cannabinoids in solution are susceptible to degradation via the action of light, temperature, and auto-oxidation. Increasing cannabinoid solubility has long been a quest with various solutions, such as salt formation, co-solvency using ethanol, propylene glycol, or PEG 400, micellization using polysorbate 80, cremophor EL, nano or micro emulsification, encapsulation in lipid based formulations, complexation with other compounds such as cyclodextrin, or conjugation to glycosides.

The above solutions still do not adequately increase solubility of cannabinoids. In particular, most of the above solutions focus on surrounding the molecular entity with other materials to increase solubility. Where the compound structure is chemically changed in an effort to achieve solubilization of the resulting compound, the results have not been encouraging. Cannabinoid-acidic salt and glycoside conjugates have yet to become popular solutions for increasing dissolution rate of cannabinoids, especially when the resulting product of ionization during dissolution does not bring out the much wanted cannabinoid.

Cannabinoid dosing remains an issue to be addressed. Cannabidiol has a recommended dosage of 500 mg-1,000 mg for a 50 kilogram (110 lbs) person, or 680 mg-1360 mg for a 150 lbs person to treat Dravet symptom, a severe form of epilepsy. This high dosage leads to liver toxicity and adverse reactions.

Increasing cannabinoid solubility while maintaining active functional groups within the cannabinoid molecule after dissolution such that the cannabinoid molecule acts like it otherwise would do remains a challenge. Increasing potency of cannabinoid while reducing dosage and toxicity is another challenge. Combining multiple cannabinoids into one chemical entity resulting in modulation of their pharmacological properties or acquisition of new properties has never been explored. This invention seeks to solve these problems.

SUMMARY

This invention relates to compounds wherein cannabinoid(s) are linked with a amine-PEG (amine-polyethylene glycol) or diamine-PEG or tri-amine linker to achieve a mono-functional or bi-functional or tri-functional cannabinoid amide-PEG, which is highly soluble and increases potency. Various reaction pathways to arrive at these compounds include through reacting cannabinoids with mPEG-amine directly or via cannabinoid-N-hydroxysuccinimide ester. The invention also discloses cannabinoid-acid-PEG ester compounds synthesized via esterification of cannabinoid acid and hydroxy-PEG. Finally, the invention discloses cannabinoid-PEG-functional group compounds synthesized via reacting halogenated cannabinoid with reactive PEG (PEG having at least one function group).

In particular, the present invention provides a compound having the formula:

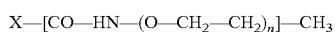

wherein X is a cannabinoid having a phenolic group, and wherein X is linked to —[CO—HN—(O—CH$_2$—CH$_2$)$_n$]—CH$_3$ at the carbon at the 2' position on the phenolic ring.

The present invention provides a compound as above, wherein n is 7 to give the formula:

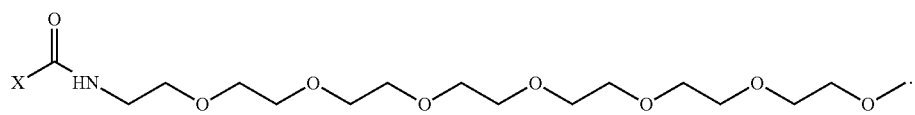

The present invention provides a compound as above, wherein X is:

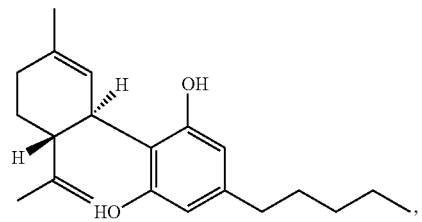

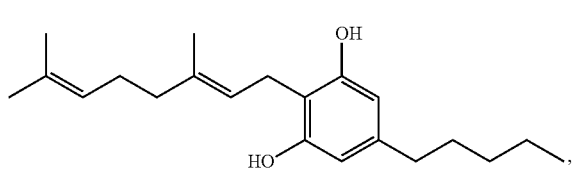

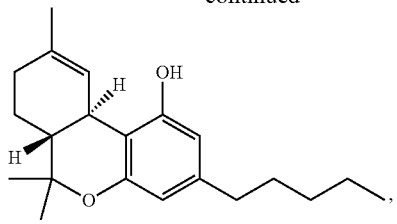

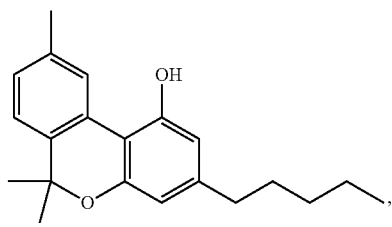

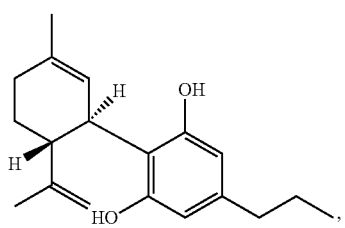

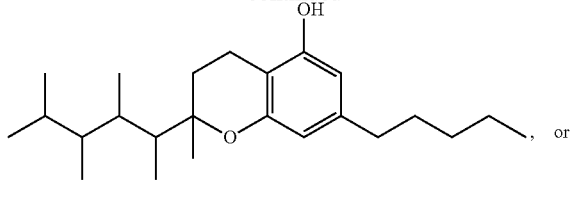, or

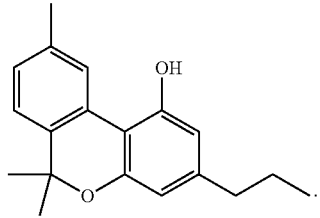.

The present invention provides a compound having the formula:

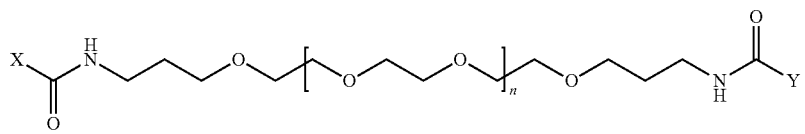

where in X is a cannabinoid having a phenolic group, wherein Y is a cannabinoid having a phenolic group and Y is different from X, wherein X is linked to —[CO—HN—(O—CH$_2$—CH$_2$)$_n$] at the carbon at the 2' position on the phenolic ring, and wherein Y is linked to —[CO—HN—(O—CH$_2$—CH$_2$)$_n$] at the carbon at the 2' position on the phenolic ring.

The present invention provides a compound as above, wherein X and Y are the same.

The present invention provides a compound as above, wherein X is:

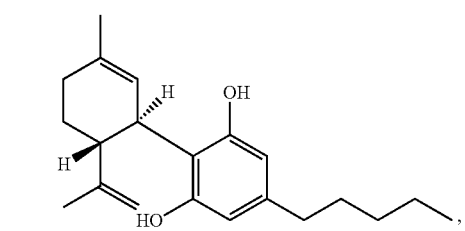,

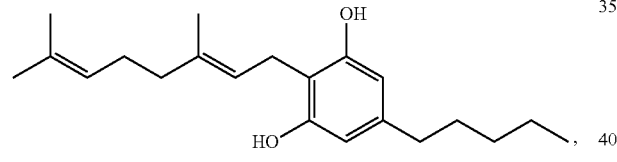,

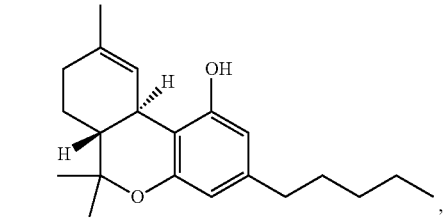,

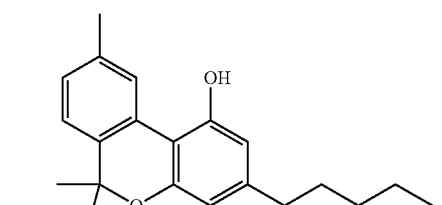,

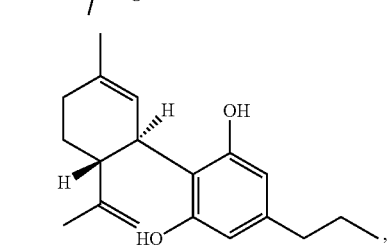,

-continued

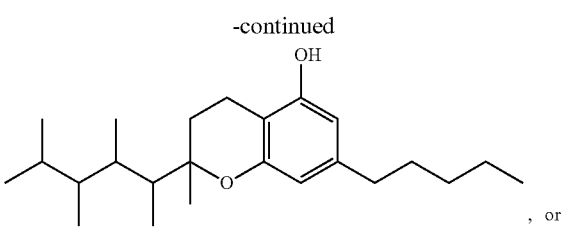, or

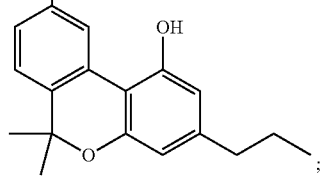;

and

Y is different from X and is one of:

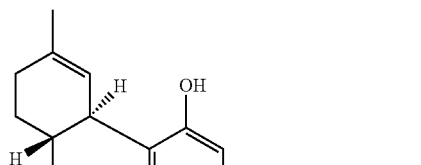,

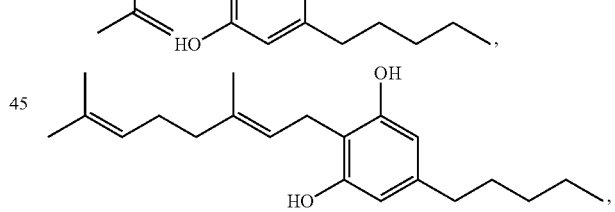,

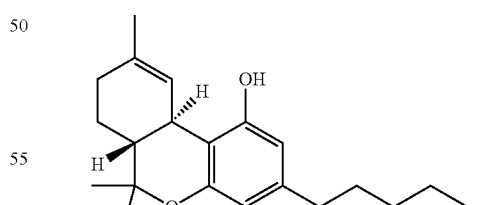,

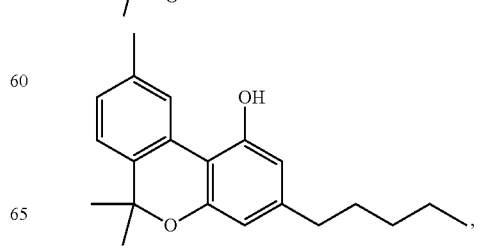,

-continued
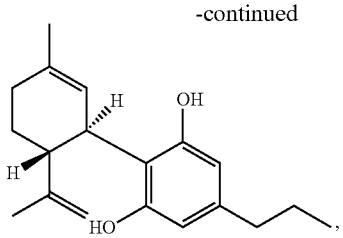
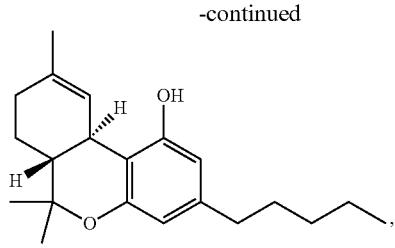
The present invention provides a compound as above, wherein X and Y are the same and are:
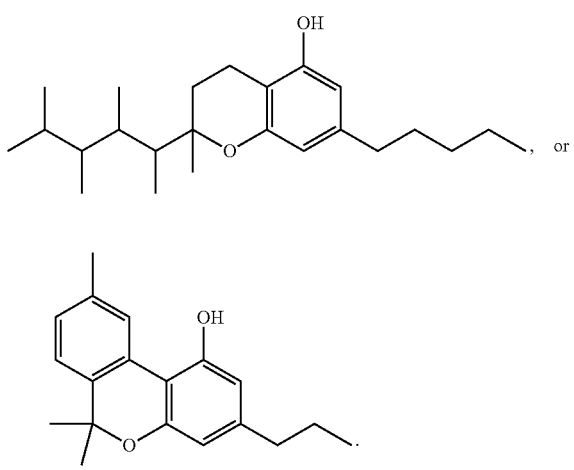
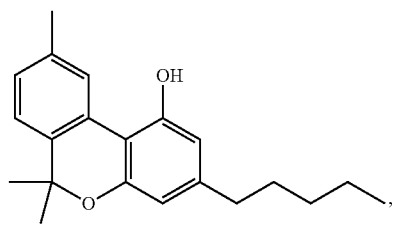
The present invention provides a compound having the formula:
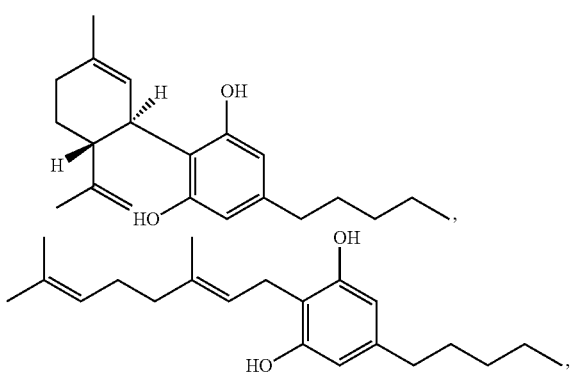
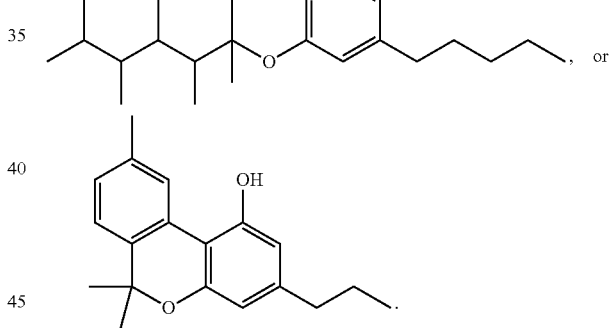
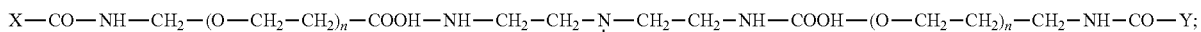
X—CO—NH—CH$_2$—(O—CH$_2$—CH$_2$)$_n$—COOH—NH—CH$_2$—CH$_2$—N—CH$_2$—CH$_2$—NH—COOH—(O—CH$_2$—CH$_2$)$_n$—CH$_2$—NH—CO—Y;
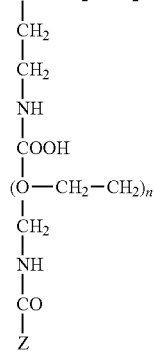

where in X is a cannabinoid having a phenolic group, wherein Y is a cannabinoid having a phenolic group and Y is different from X, wherein Z is a cannabinoid having a phenolic group and Z is different from X and Y, wherein X is linked to —[CO—HN—(O—CH$_2$—CH$_2$)$_n$] at the carbon at the 2' position on the phenolic ring, wherein Y is linked to —[CO—HN—(O—CH$_2$—CH$_2$)$_n$] at the carbon at the 2' position on the phenolic ring, and wherein Z is linked to —[CO—HN—(O—CH$_2$—CH$_2$)$_n$] at the carbon at the 2' position on the phenolic ring.

The present invention provides a compound as above, wherein X, Y, and Z are:

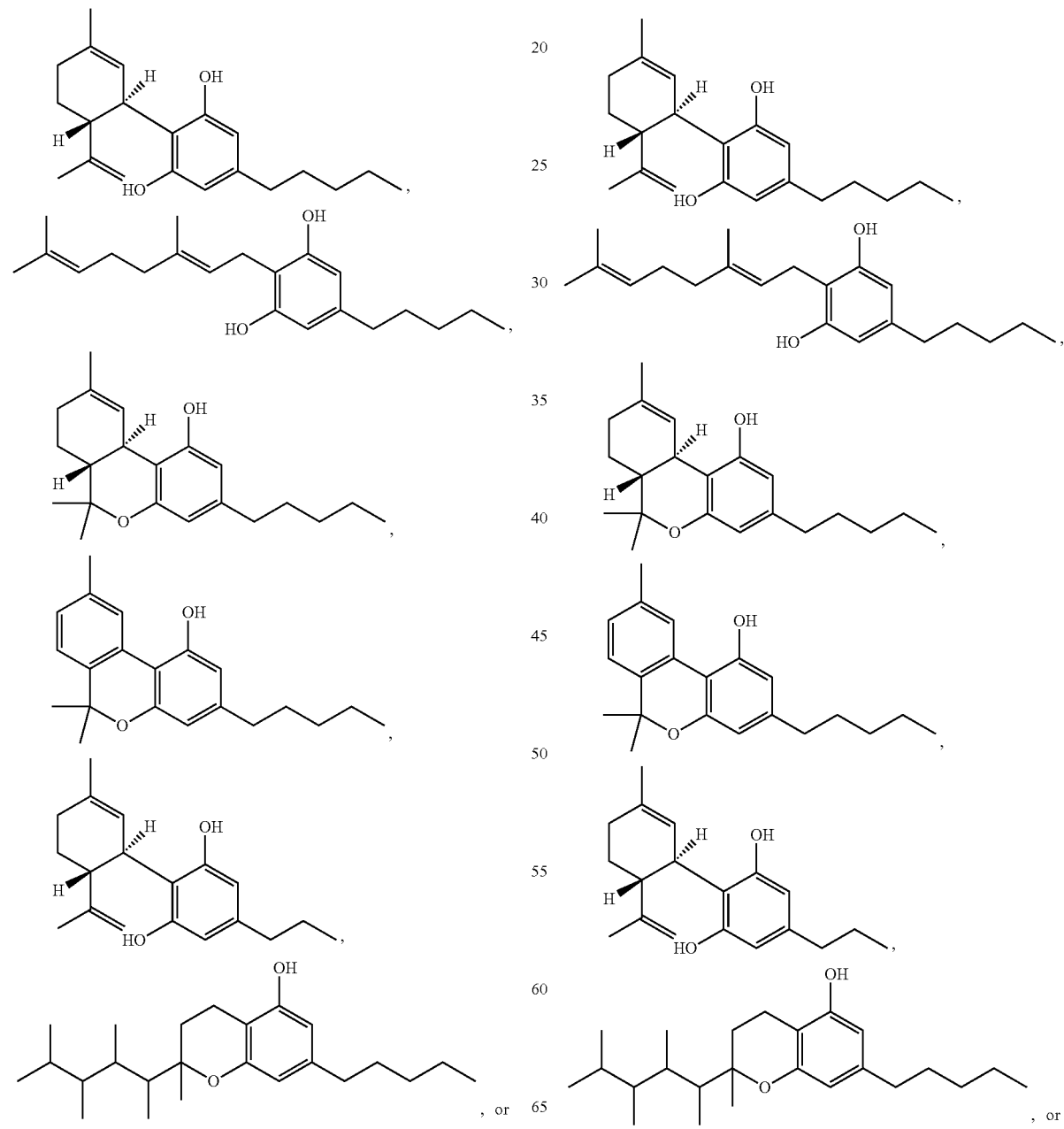

-continued

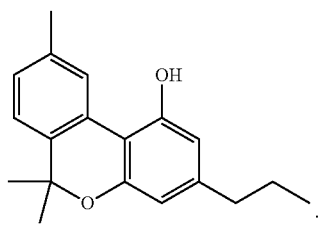

The present invention provides a compound as above, wherein X, Y, and Z are the same cannabinoid.

The present invention provides a compound as above, wherein X, Y, and Z are:

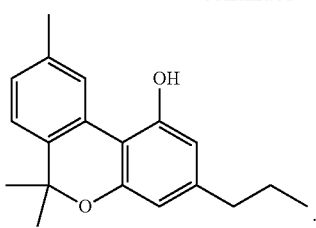

The present invention provides a compound as above, wherein two of X, Y, and Z are the same cannabinoid and the third is a different cannabinoid.

The present invention provides a compound as above, wherein X, Y, and Z are:

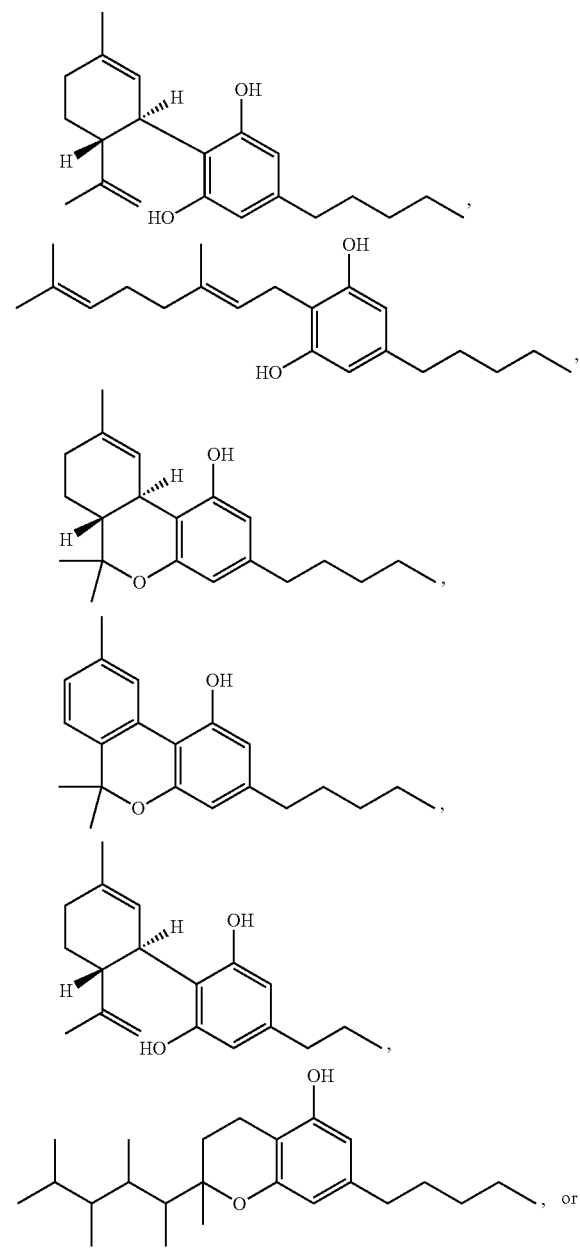

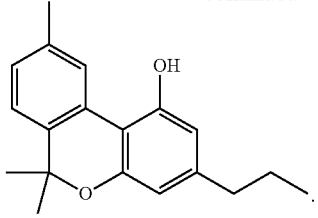

The present invention provides a compound having the formula:

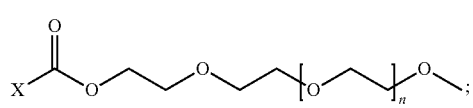

wherein X is a cannabinoid having a phenolic group, and wherein X is linked to —[COO—(O—CH$_2$—CH$_2$)$_n$] at the carbon at the 2' position on the phenolic ring.

The present invention provides a compound as above, wherein X is:

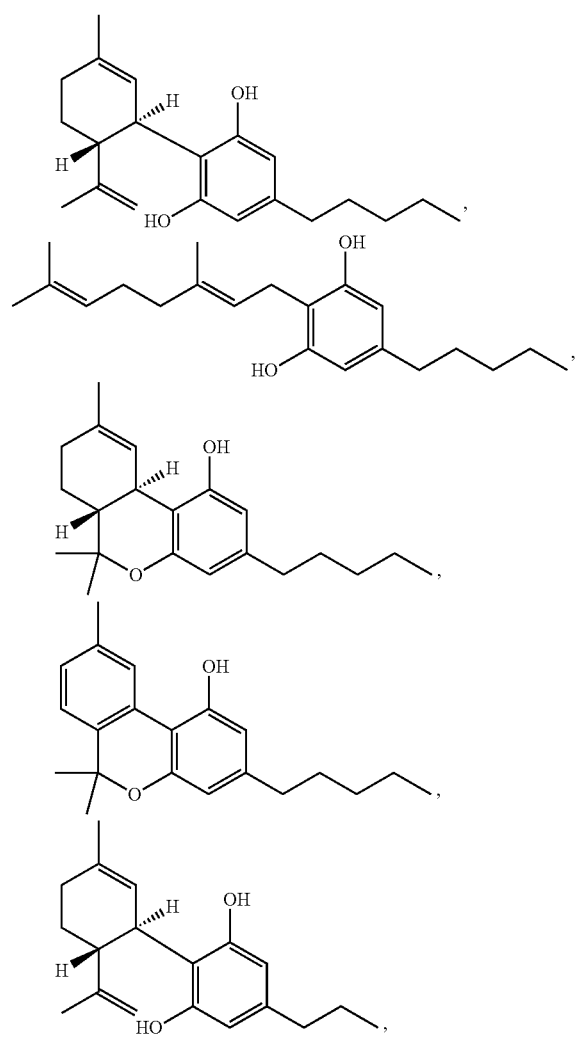

-continued

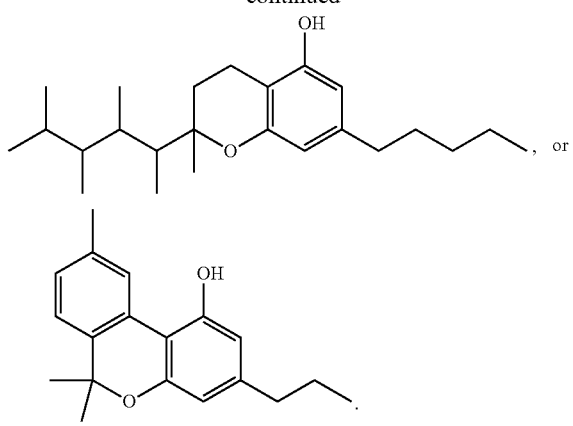
, or

The present invention provides a compound having the formula:

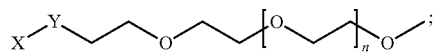

wherein X is a cannabinoid having a phenolic group, wherein Y is an amine, hydroxy, or sulfhydryl group, and wherein X is linked to —[Y—(O—CH$_2$—CH$_2$)$_n$] at the carbon at the 2' position on the phenolic ring.

The present invention provides a compound as above, wherein X is:

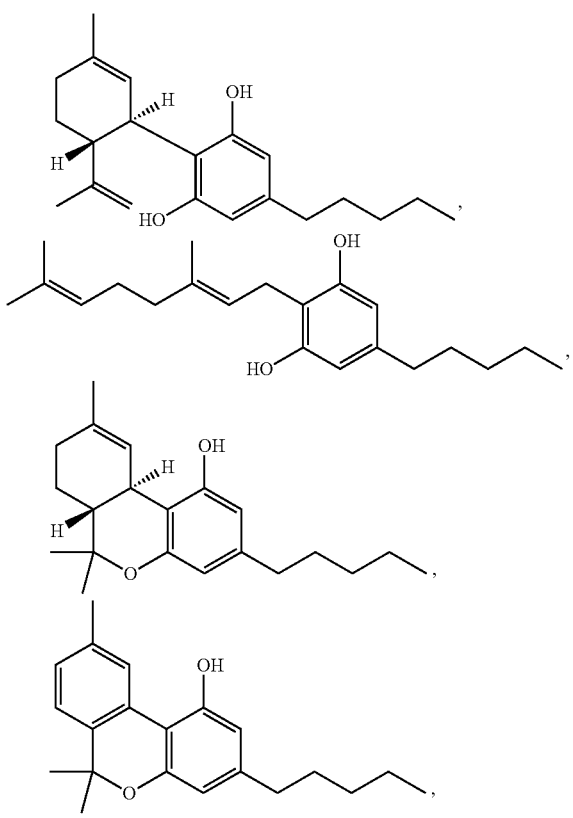
, or

ABBREVIATIONS

API: Active Pharmaceutical Ingredient
CBC: Cannabichromene
CBD: Cannabidiol
CBDA: Cannabidiolic Acid
CBDV: Cannabidivarin
CBG: Cannabigerol
CBN: Cannabinol
CBV: Cannabivarin
Da: Dalton
DCC: N,N'-dicyclohexylcarbodiimide
DCM: Dichloromethane
DMF: N,N'-dimethylformamide
IUPAC: International Union of Pure and Applied Chemistry
lbs: pounds
mg: milligram
μg: microgram
NHS: N-hydroxysuccinimide
NMR: Nuclear Magnetic Resonance
OA: Olivetolic Acid
OA-NHS: Olivetolic Acid-N-hydroxysuccinimide
PEG: Polyethylene Glycol
pTSA: Para-toluene Sulfonic Acid
RPM: Round Per Minute
THC: Δ$^9$-tetrahydrocannabinol
TLC: Thin-layer Chromatography

DETAILED DESCRIPTION OF CERTAIN INVENTIVE EMBODIMENTS

Figure 1:
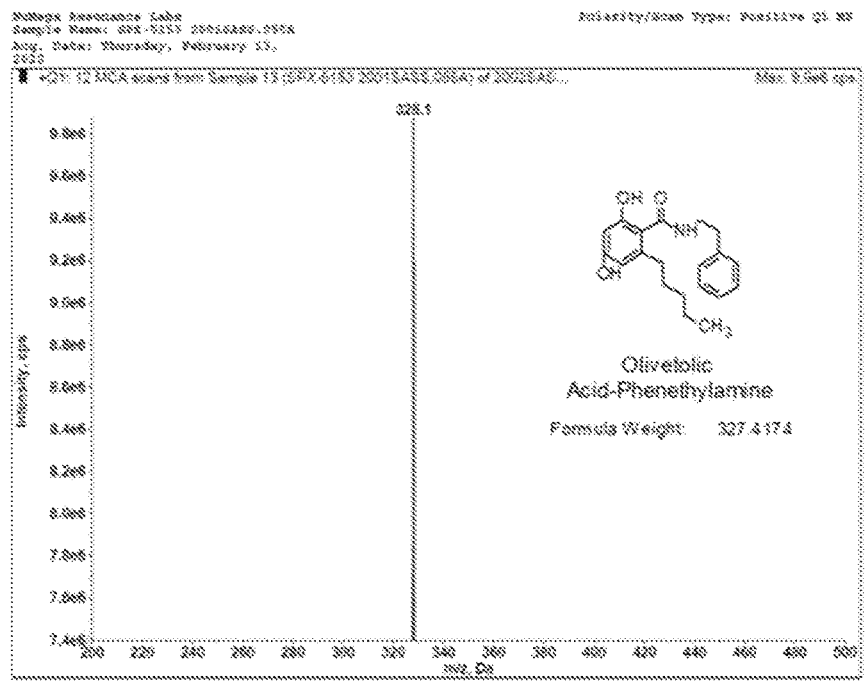
FIG. 1 is the mass spectrometry plot of olivetolic acid phenethylamine adduct produced by an experiment described herein.

This present invention is capable of being embodied in various forms. The description below of several embodiments is made with the understanding that the present disclosure is to be considered as an exemplification of the claimed subject matter, and is not intended to limit the attached claims to the specific embodiments illustrated. The headings used throughout this disclosure are provided for convenience only and are not to be construed to limit the claims in any way. Embodiments illustrated under any heading may be combined with embodiments illustrated under any other heading.

As used herein, the verb "to comprise" in this description, claims, and other conjugations are used in its non-limiting sense to mean those items following the word are included, but items not specifically mentioned are not excluded.

Reference to an element by the indefinite article "a" or "an" does not exclude the possibility that more than one of the elements are present, unless the context clearly requires that there is one and only one of the elements. The indefinite article "a" or "an" thus usually means "at least one." Additionally, the words "a" and "an" when used in the present document in concert with the words "comprising" or "containing" denote "one or more."

The word "cannabinoid" used in this description, claims, and other conjugations is used to mean any compound that interacts with a cannabinoid receptor and other cannabinoid mimetics, including, but not limited to, certain tetrahydropyran analogs ($\Delta^9$-tetrahydrocannabinol, $\Delta^8$-tetrahydrocannabinol, 6,6,9-trimythel-3-pentyl-6H-dibenzo[b,d]pyran-1-ol,3-(1,1-dimethylheptyl)-6,6a7,8, 10, 10a-hexahydro-1-1hydroxy-6,6-dimythel-9H-dibezo[b,d]pyran-9-ol, (-)-(3S,4S)-7-hydroxy-delta-6-tetrahydrocannabinol-1,1-dimethylheptyl, (+)-(3S,4S)-7-hydroxy-$\Delta$-6-tetrahydrocannabinol, and $\Delta^8$-tetrahydrocannabinol-11-oic acid); certain open pyran-ring analogs (e.g., 2-[3-methyl-6-(1-methylethenyl-2-cyclohexen-1-yl]-5-pentyl-1, 3-benzendi-ol, and 4-(1,1-dimethylheptyl)-2,3'-dihydroxy-6'-α-(3-hydroxypropyl)-1',-2',3',4',5',6'-hexahydrobiphenyl), their salts, solvates, metabolites, and metabolic precursors.

Embodiments of this application relate to at least one cannabinoid chemically linked to at least one polyethylene glycol (PEG) linker, which may have one or more amine groups. Where there are more than one cannabinoid, the cannabinoids may be the same or different from each other.

Polyethylene glycol (PEG) is a polyether compound with many applications. The chemical formula of PEG is expressed as $H-(O-CH_2-CH_2)_n-OH$, with "n" being an integer. The value of n determines the number of repetition of the group $[-(O-CH_2-CH_2)-]$. PEG therefore has a molecular weight depending on the value of n. Commonly known are PEG 7, PEG 40, PEG 400, with a variety of uses in medical, pharmaceutical, cosmetics, food, and industrial application.

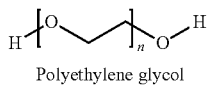

Polyethylene glycol

PEG is highly hydrophilic and dissolves readily in water. Moreover, it has low toxicity and is consumable orally. The functional groups at either end of the PEG molecule may be substituted with other functional groups, such as amine, which may have stronger reactivity and causes PEG-amine to react and ultimately link to another molecule to form a new molecular entity. Amino-PEG-hydroxyl ($NH_2$-PEG-OH) is a product where the hydrogen (H) on one end of the PEG molecule has been substituted by an amine group ($-NH_2$). Diamine PEG is a molecule of PEG with functional groups at both ends substituted by amine groups, resulting in a molecule of the formula $H_2N$-PEG-$NH_2$. Other functional groups may also be substituted in, such as azide ($-N_3$), phosphate, biotin, carboxyl group ($-COOH$), bromine, among other functional groups.

Amino-PEG is a popular linker due to the reactivity of the amino group at the end of the PEG chain. Where the goal is one cannabinoid linked with one PEG chain, then the chosen PEG should have one reactive group. Where the goal is a bifunctional cannabinoid-PEG linked molecule, a PEG-compound with two reactive groups is required. For example, diamine-PEG may also be used, such that the resulting molecule from the linkage reaction has two cannabinoids attached to each side of the PEG-based molecule. In this case, the resulting molecule may be a homo-bifunctional cannabinoid, such that there are two cannabinoids of the same kind on each side of the PEG linker, or heterobifunctional cannabinoid, such that there are two cannabinoids of different kinds on each side of the PEG linker.

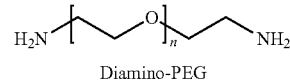

Diamino-PEG

In embodiments, mPEG-amine may also be used to "PEGylate" carboxylic groups of active pharmaceutical ingredients (APIs). mPEG-amine is a key intermediate to prepare specific functionalized activated mPEGs. The use of mPEG-amine instead of mPEG-alcohol improves the physiological stability of the mPEG-drug conjugate (e.g. amide instead of an ester bond). Although mPEG-alcohol may form hydrolysable ester bond that can be useful in prodrug cannabinoid formulation, i.e. cannabinoid is made more water soluble by attaching ester PEG, once in the body the ester bond is cleaved by endogenous esterases to release native cannabinoid.

In embodiments described herein, mPEG-amine, which is represented as $H_2N-(O-CH_2-CH_2)_n-CH_3$, may be linked to a cannabinoid, for example cannabidiol, to improve solubility. mPEG-amine is chosen for linking due to the improved physiological stability of the mPEG-drug conjugate.

The amine-PEG used in these reactions may have any value of n in the $[-(O-CH_2-CH_2)-]_n$ group. However, smaller value of n equates smaller molecular weight. At the same time, a longer chain of PEG, meaning a higher value of n, may give more space for the various cannabinoids to link to both ends of the PEG chain. In the example below, n is 7, such that the molecule used is mPEG7-amine.

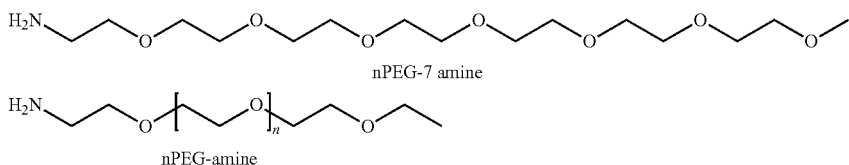
nPEG-7 amine

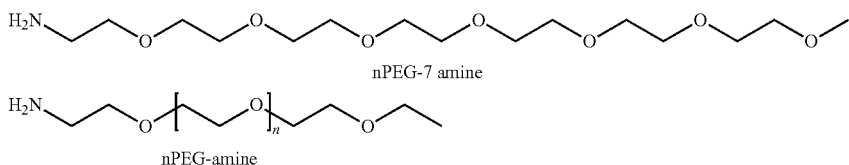
nPEG-amine

While linking a cannabinoid to a PEG-molecule may improve solubility, it is imperative that the cannabinoid molecule retains its functional groups and the cannabinoid-PEG molecules operate in the same manner as cannabinoids in vivo. Functional groups on cannabinoid molecules are alcoholic groups, in particular the —OH group on the phenolic group that is common to natural cannabinoid molecules that are tetrahydropyran ring analogs or open pyran ring analogs. Linking PEG to a cannabinoid molecule must take into account this particular feature.

In embodiments, the solution offered by this invention is the use of the acidic version of cannabinoid molecules for linkage with PEG. Cannabinoids are present in cannabis plants as cannabinoid acids. For example, delta-9-tetrahydrocannabinoid is present as delta-9-tetrahydrocannabinolic acid in cannabis plants. This is also true for cannabidiolic acid, cannabigerolic acid, cannabinolic acid, cannabidivarinic acid, cannabichromenic acid, cannabivarinic acid, and other cannabinoid acids.

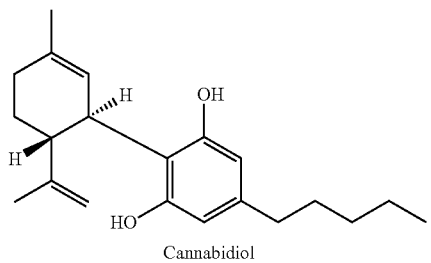
Cannabidiol

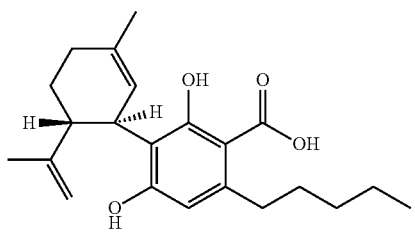
Cannabidiolic acid

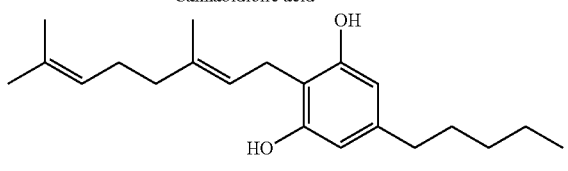
Cannabigerol

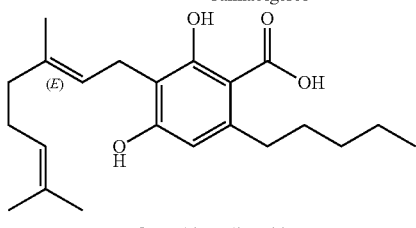
Cannabigerolic acid

-continued

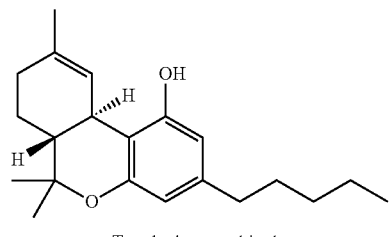
Tetrahydrocannabinol

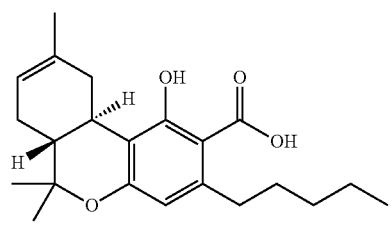
Tetrahydrocannabinolic acid

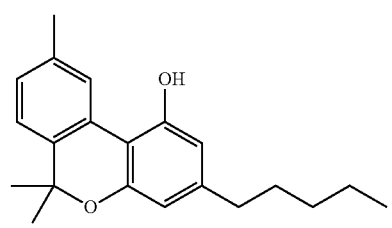
Cannabinol

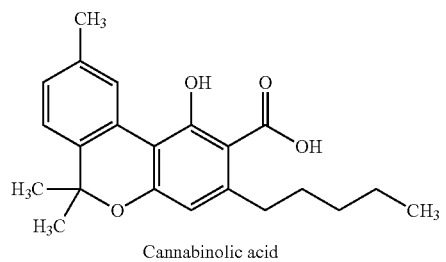
Cannabinolic acid

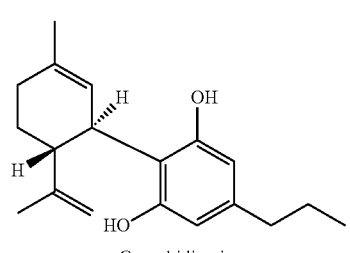
Cannabidivarin

-continued

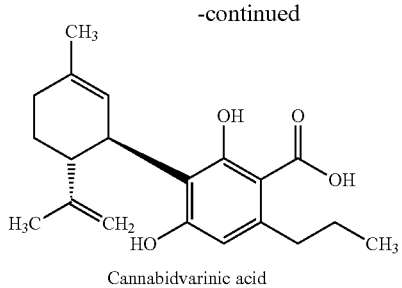
Cannabidvarinic acid

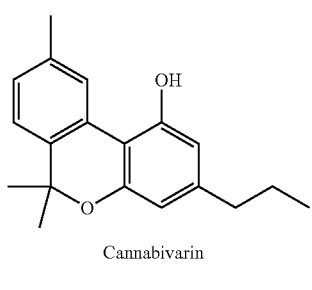
Cannabichromene

Cannabichromenic acid

Cannabivarin

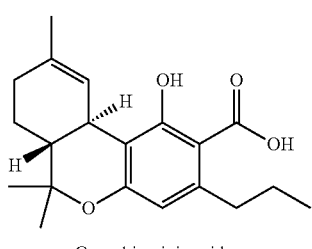
Cannabivarinic acid phenolic ring. This carbon numbering is according to the IUPAC system. Reaction between the carboxyl group on the cannabinoid acid and another function group on the PEG linker, such as an amine group, is easier to create. The result also preserves the cannabinoid molecule, in particular the functional groups on the cannabinoid molecules. In the cannabidiolic acid molecule, the carboxylic group is not part of the cannabidiol molecule:

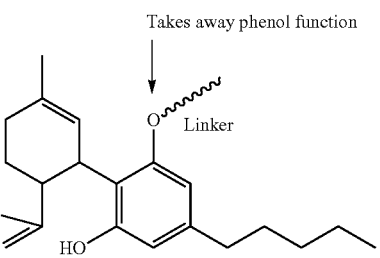

Linking a PEG-molecule to a cannabidiolic acid molecule at the carboxylic group thus has the potential of preserving the cannabinoid molecule as a whole, instead of linking PEG to a functional group directly on the cannabinoid molecule, such as the phenol function group (—OH) on the phenolic ring like below:

In embodiments, a cannabinoid-PEG linked molecule with increased solubility may be a monofunctional cannabinoid-PEG linked molecule expressed as:

Cannabinoid acid-amino-(O—CH$_2$—CH$_2$)$_n$—CH$_3$ or

X—[CO—HN—(O—CH$_2$—CH$_2$)$_n$]—CH$_3$ wherein X is a cannabinoid having a phenolic group, and wherein X is linked to —[CO—HN—(O—CH$_2$—CH$_2$)$_n$]—CH$_3$ at the carbon at the 2' position on the phenolic ring, such as:

Cannabinoid acids are characterized by the presence of the carboxyl group —COOH at the 2' carbon position on the phenolic ring. The 2' carbon position means the 1' carbon position is where the functional group —OH attaches to the

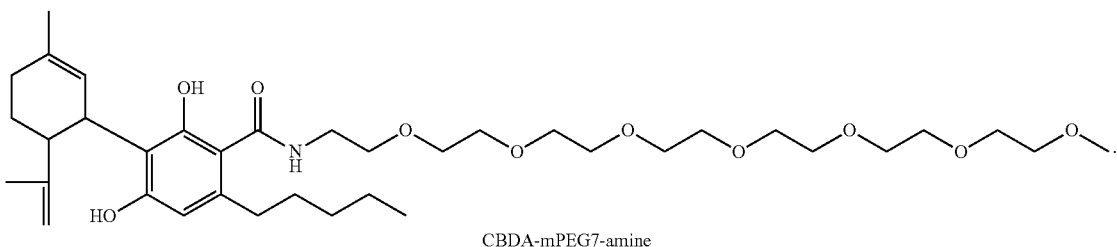 [SMILES: C=C(C)C1CCC(C)=CC1c1c(O)cc(CCCCC)c(C(=O)NCCOCCOCCOCCOCCOCCOCCOC)c1O]
CBDA-mPEG7-amine

X is a cannabinoid having a phenolic group. X may be, but is not limited to, anyone of these:

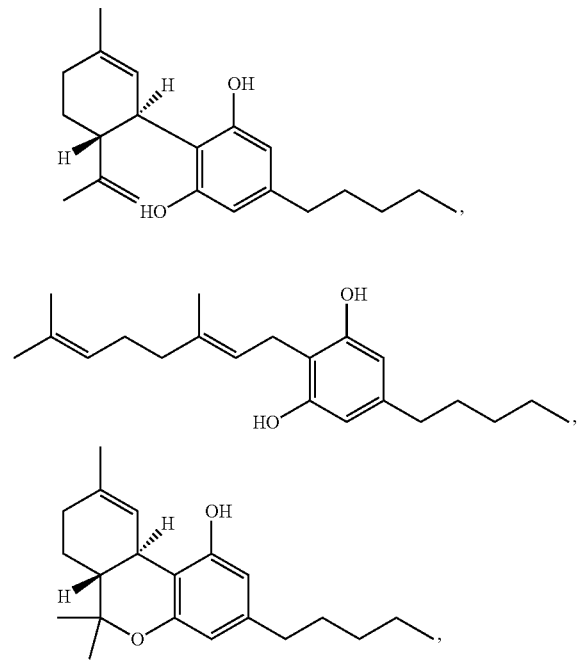

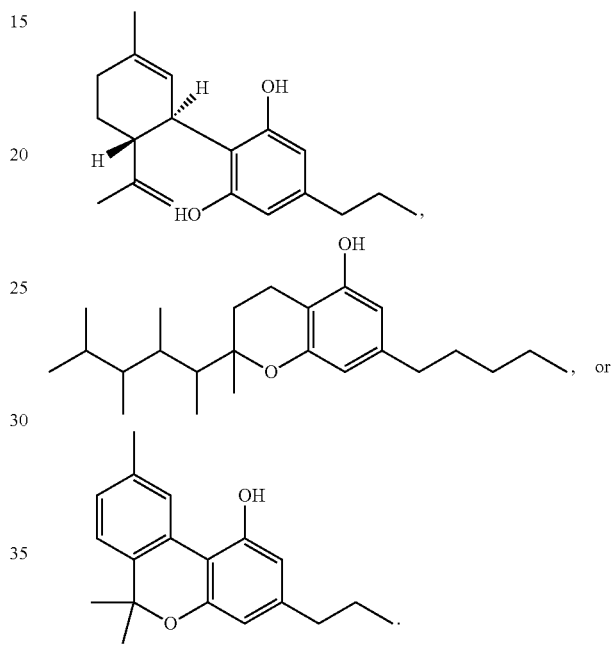

In embodiments, a cannabinoid-PEG linked molecule may also be a bifunctional cannabinoid-PEG linked molecule expressed as:

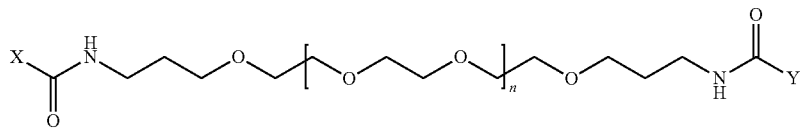

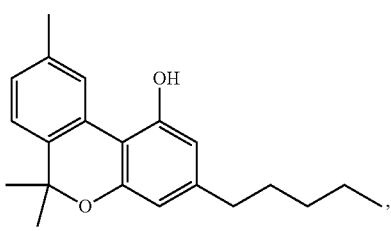

wherein X is a cannabinoid having a phenolic group,
wherein Y is a cannabinoid having a phenolic group,
wherein X is linked to —[CO—HN—(O—CH$_2$—CH$_2$)$_n$] at the carbon at the 2' position on the phenolic ring, and
wherein Y is linked to —[CO—HN—(O—CH$_2$—CH$_2$)$_n$] at the carbon at the 2' position on the phenolic ring; X and Y can be the same cannabinoid or different cannabinoids.

In embodiments, a cannabinoid-PEG linked molecule may also be a homobifunctional cannabinoid-PEG linked molecule expressed as:

cannabinoid acid-amine-(O—CH$_2$—CH$_2$)$_n$-amine-cannabinoid acid the two cannabinoids are the same, such as:

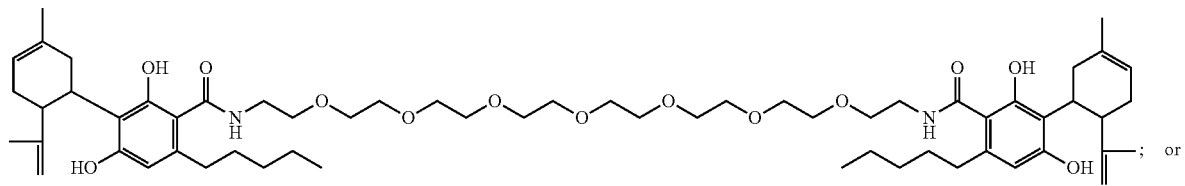

CBDA-diamino PEG7-CBDA

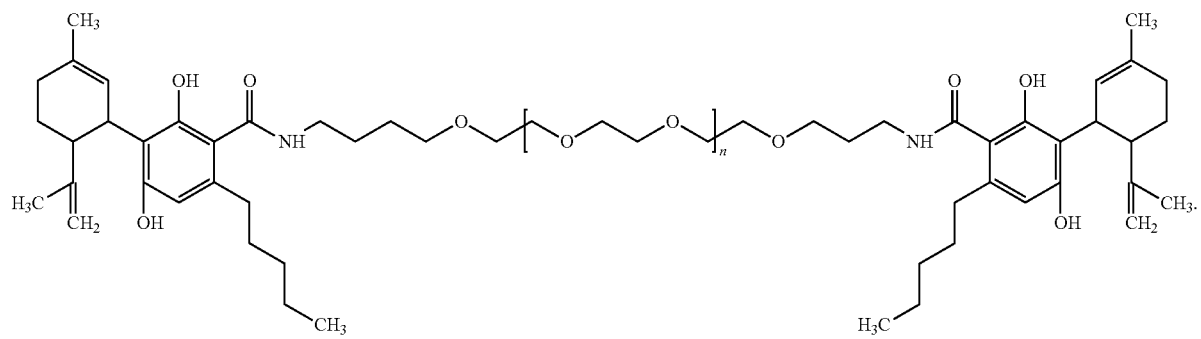

CBD-diamino PEG-CBDA

In embodiments, a cannabinoid-PEG linked molecule may also be a heterobifunctional cannabinoid-PEG linked molecule expressed as:

cannabinoid acid-amine-(O—CH$_2$—CH$_2$)$_n$-amine-different cannabinoid acid or

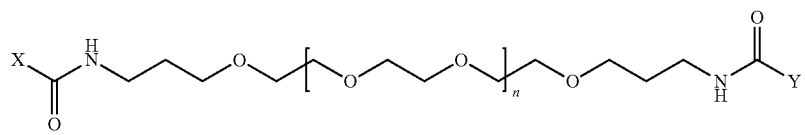

wherein the two cannabinoids are different, such as:

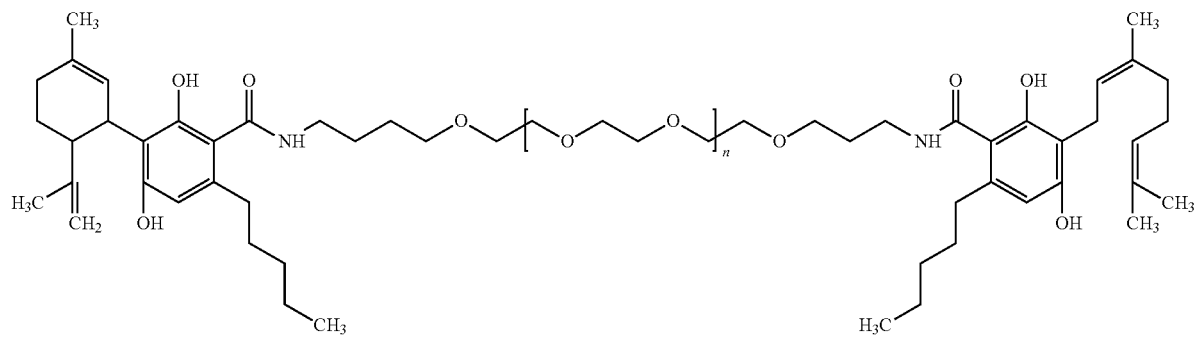

X and Y may be, but are not limited to, anyone of these:
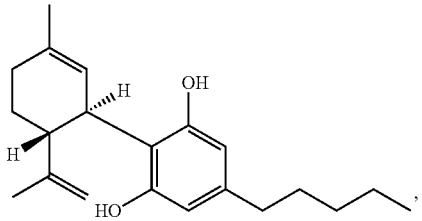
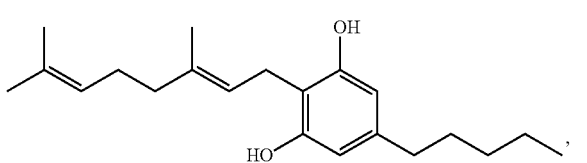
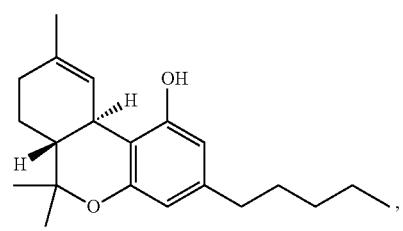
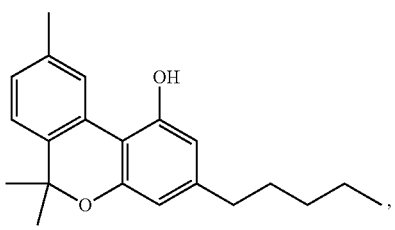
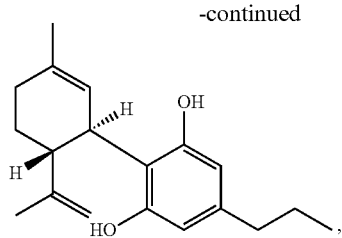
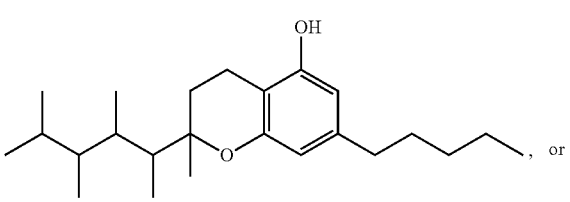
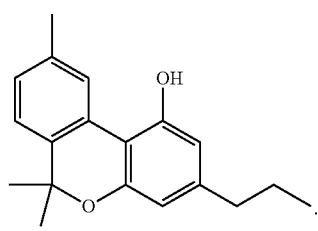
In embodiments, a cannabinoid-PEG linked molecule may also be a trifunctional cannabinoid-PEG linked molecule expressed as:
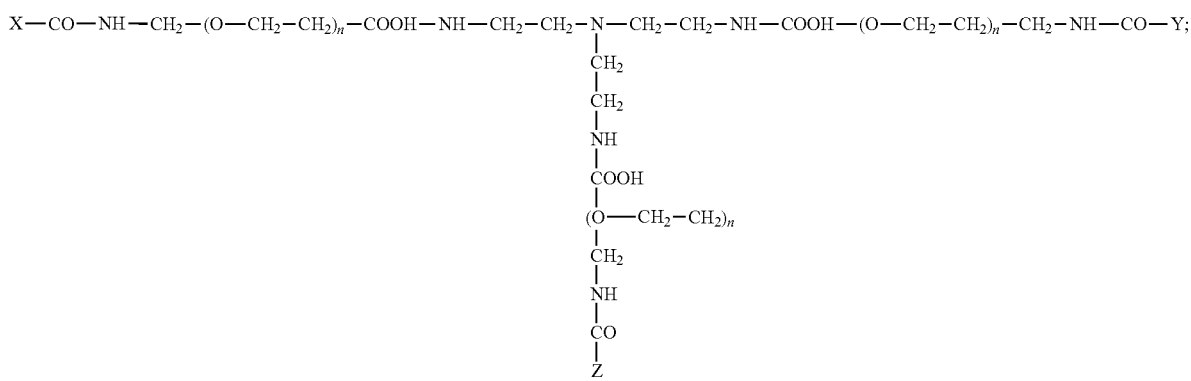

with, X, Y and Z being cannabinoids having a phenolic group, and X, Y, and Z are different cannabinoids, wherein X is linked to —[CO—HN—(O—CH$_2$—CH$_2$)$_n$] at the carbon at the 2' position on the phenolic ring, wherein Y is linked to —[CO—HN—(O—CH$_2$—CH$_2$)$_n$] at the carbon at the 2' position on the phenolic ring, and wherein Z is linked to —[CO—HN—(O—CH$_2$—CH$_2$)$_n$] at the carbon at the 2' position on the phenolic ring.

Alternatively, two of X, Y, and Z may be the same but the third one is a different cannabinoid. Finally, X, Y and Z may be the same cannabinoid. X, Y, and Z may be, but are not limited to, anyone of these:

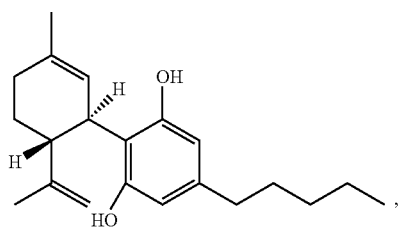

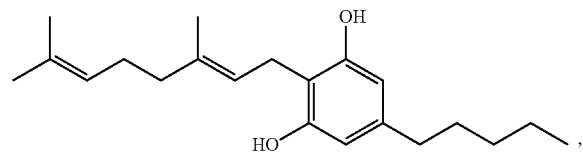

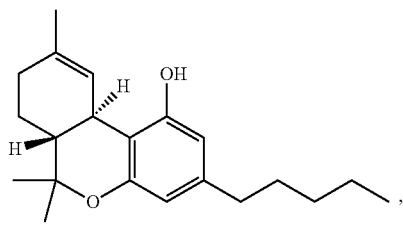

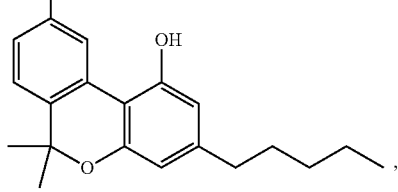

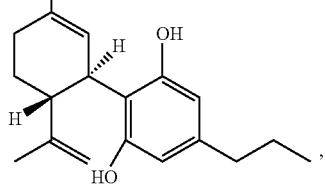

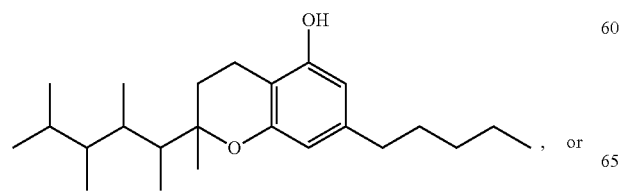, or

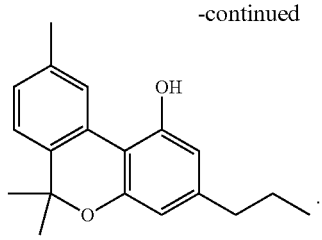

In embodiments, a cannabinoid-PEG linked molecule may also be a cannabinoid-functional PEG linked molecule expressed as:

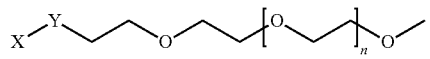

with X being a cannabinoid having a phenolic group, Y being an amine, hydroxy, or sulfhydryl group and X is linked to —[Y—(O—CH$_2$—CH$_2$)$_n$] at the carbon at the 2' position on the phenolic ring.

X may be, but is not limited to, anyone of these:

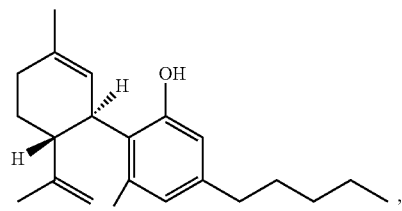

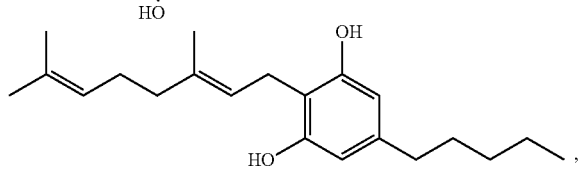

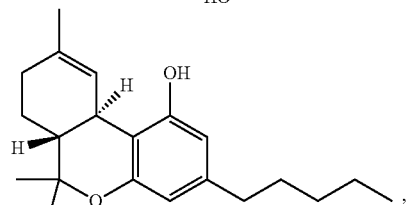

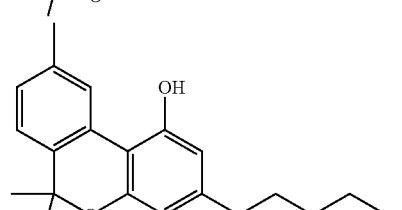

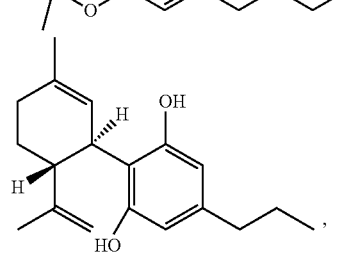

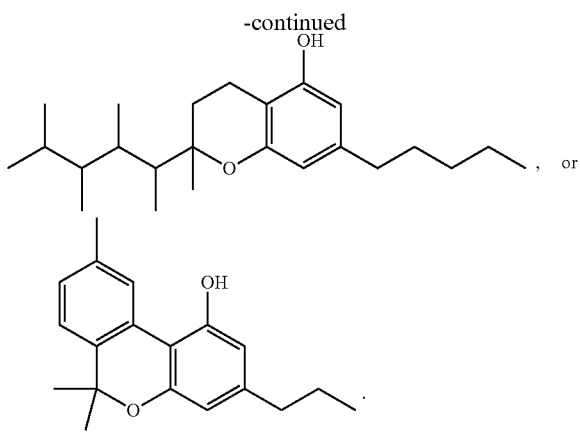
, or

In all embodiments, the PEG linker may have different values of repeating units of —(O—CH$_2$—CH$_2$)$_n$. In other words, the value of n in the PEG repetitive unit —(O—CH$_2$—CH$_2$)$_n$— may be any integer that realistically exists among the known PEG molecules. For illustrative purposes, mPEG-7 was used in the example provided below since mPEG-7 is readily available and is known to be stable in reactions.

Reaction Pathway Determination

To determine the best pathway to react PEG-amine with a cannabinoid acid, experiments were conducted using olivetolic acid. Olivetolic acid has a similar structure with cannabidiol with a phenolic ring and a 5-carbon chain at the 3' carbon position on the phenolic ring, with a carboxylic group at the 2' carbon position on the phenolic ring, with an alcoholic group on the 5' position on the phenolic ring, but without the open pyran ring and other components of the cannabidiolic acid molecule. Essentially, olivetolic acid has the structure and function groups that are similar to the structure of function groups of cannabidiolic acid, where the structure and groups are the reactive sites.

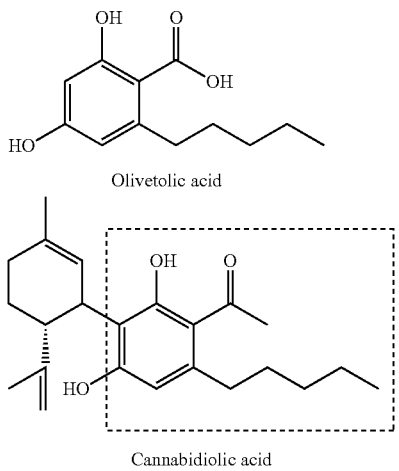

Experiments were conducted to link olivetolic acid with an amine, either directly or through an intermediated. Two pathways were explored: linking olivetolic acid with phenethylamine, an amine, directly, or linking olivetolic acid with phenethylamine via an active ester, in this case olivetolic-N-hydroxysuccinimide (NHS) ester.

Procedure for Direct Linking of Olivetolic Acid with Phenethylamine:

Olivetolic acid (OA, 32 mg, 0.14 mmols) is dissolved in 1 mL of anhydrous dichloromethane (DCM) (solvent) in a flame-dried glass vial equipped with a magnetic stir bar under atmosphere of nitrogen. To the solution of OA was added phenethylamine (34 mg, 0.28 mmols, 2 mol equivalents relative to OA), N,N'-dicyclohexylcarbodiimide (DCC, 35 mg, 0.17 mmols) (reactant) and para-toluene sulfonic acid (pTSA, 5 mg, 0.025 mmols) (catalyst) were added sequentially to OA solution. The reaction was stirred at room temperature for 1 hour under atmosphere of nitrogen. The solvent was evaporated under reduced pressure, re-dissolved in toluene, filtered through a short pad of Celite filtering material and purified by column chromatography on silicagel eluting with 3:1 hexanes:ethyl acetate. Pure olivetolic acid-phenethylamine linked product was obtained at 75% yield.

Reaction Scheme:

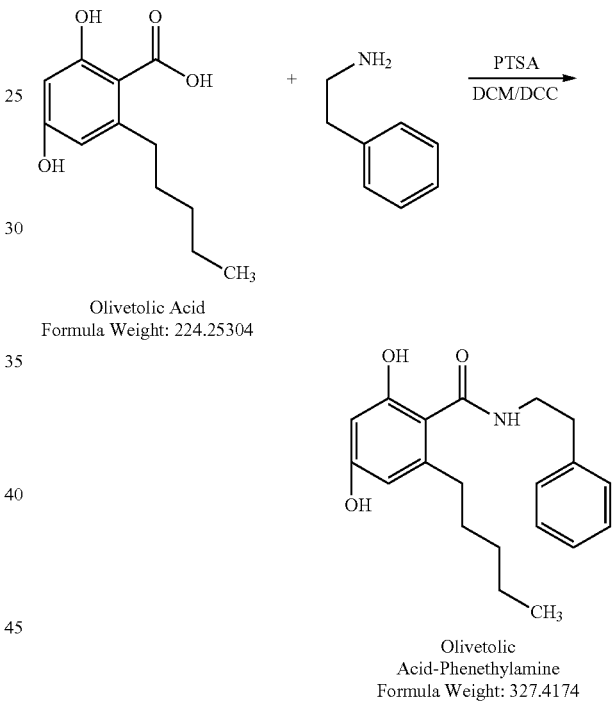

Figure 2:
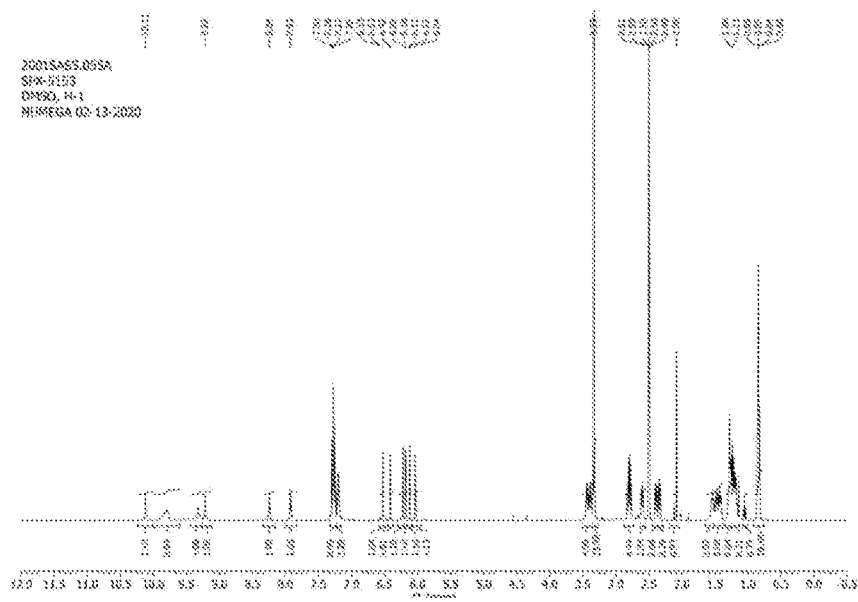
FIG. 2 is the NMR spectrum plot of olivetolic acid phenethylamine adduct produced by the same experiment as in FIG. 1.

Identity of olivetolic acid-phenethylamine was verified by mass spectrum, the result is in FIG. 1. NMR of olivetolic acid-phenethylamine is in FIG. 2.

Procedure for Linking of Olivetolic Acid with Phenethylamine Via NHS Ester:

Dissolve N-hydroxysuccinimide (NHS, 20 mg, 0.18 mmols, 1.3 molar equivalents over OA) (reactant) in 40 μL of dry N,N'-dimethylformamide (DMF) (solvent) in a 10 mL flame-dried vial equipped with a magnetic stir bar. To the mixture above, add N,N'-dicyclohexylcarbodiimide (DCC, 48 mg, 0.24 mmols, 1.76 molar equivalents over OA) (reactant). Quickly stir to dissolve. Olivetolic acid (OA, 30 mg, 0.13 mmols) was then added under a blanket of nitrogen. The reaction was stirred for 2 hours at room temperature. The precipitated material was separated by centrifugation at 4° C. for 10 minutes at 10,000 RPM. The supernatant was diluted with ethyl acetate and washed twice with saturated sodium chloride. The organic layer was dried over magnesium sulfate (MgSO$_4$) and evaporated to dryness under reduced pressure. The residue was purified to give stable 33 mg of OA-NHS active ester (80% yield).

The OA-NHS active ester was used in the next step for conjugation with phenethylamine. To do so, OA-NHS active ester (20 mg, 0.06 mmols) was dissolved in 300 μL of 1,4-dioxane and phenethylamine (12 mg, 0.1 mmols, 1.7 molar equivalents) was added followed by 100 μL of 0.5M borate buffer at pH 10. After 1 hour stirring at room temperature the reaction was tested by thin-layer chromatography (TLC) in 2:1 hexanes/acetone. The spot corresponding to starting OA-NHS disappeared and a spot corresponding to the product OA-phenethylamine appeared, indicating completeness of the reaction. The reaction mixture was evaporated to dryness, then re-dissolved in ethyl acetate and washed sequentially with 1M HCl and saturated sodium chloride. The organic layer was dried over magnesium sulfate (MgSO$_4$) and evaporated to dryness. The product was isolated by column chromatography on silica gel eluting with a gradient of hexanes/ethyl acetate to give 15 mg of Olivetolic Acid-phenethylamine adduct (76% yield).

Reaction Scheme:

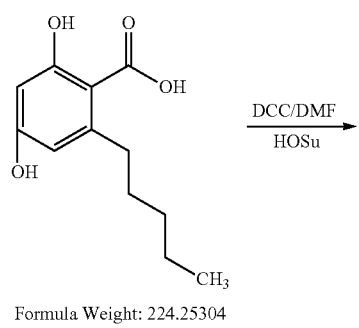

Formula Weight: 224.25304

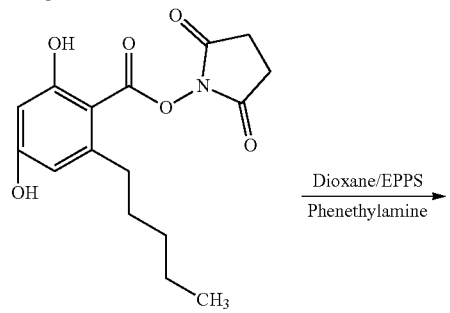

Olivetolic Acid-NHS
Formula Weight: 321.32516

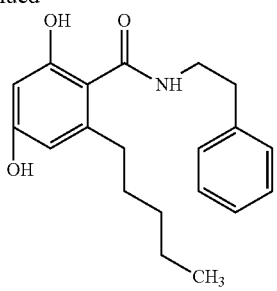

Olivetolic Acid-Phenethylamine
Formula Weight: 327.4174

Synthesis of PEG-7 Linked CBDA by Direct Conjugation

Direct conjugation of CBDA with PEG-7 is achieved by reacting CBDA with mPEG7-amine, which has one amine reactive group at one end and a —CH$_3$ group at the other end with the number of repetitive unit [—(O—CH$_2$—CH$_2$)—] at 7. Anhydrous dichloromethane (DCM), as solvent, N,N'-dicyclohexylcarbodiimide (DCC), as a reactant, and p-toluene sulfonic acid (pTSA), as the catalyst, are used in this reaction. The side product of the reaction is N,N-dicyclohexylurea.

To a stirred solution of cannabidiolic acid (CBDA, 31.9 mg, 0.089 mmols) dissolved in 3.1 mL of anhydrous dichloromethane (DCM) in flame-dried glass vial equipped with a magnetic stir bar, m-PEG7-amine (60.4 mg, 0.178 mmols, 2 molar equivalents over CBDA), N,N'-dicyclohexylcarbodiimide, (DCC, 22 mg, 0.106 mmols) was added, then p-toluene sulfonic acid (pTSA, 3.2 mg, 0.016 mmols) was added in a sequential fashion. The reaction was stirred overnight at room temperature under an atmosphere of nitrogen to keep the reaction dry. The solvent was evaporated to dryness on a roto-evaporator. The residue was resuspended in toluene, and the solution was cooled at −20° C. overnight. The precipitated side-product N,N-dicyclohexylurea was filtered through a short pad of Celite filtering material. The filtrate was evaporated to dryness and purified by column chromatography on silica gel eluting with a gradient of 7:3 to 1:1 hexanes/acetone to give desired product in 72% yield. The mass spec and NMR data showed the correct product with a mass of 679 Da.

The reaction above may be described in this CBDA-mPEG7 reaction scheme:

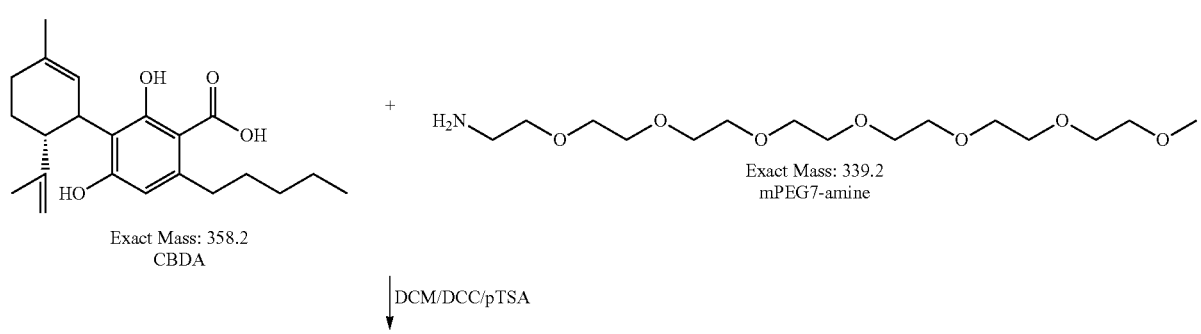

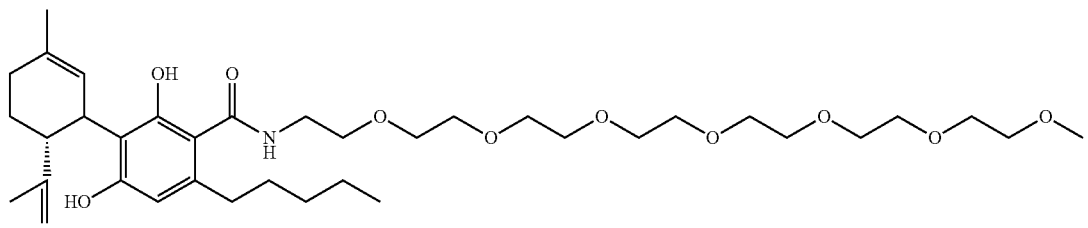

Exact Mass: 679.4
CBDA-mPEG7

Figure 3:
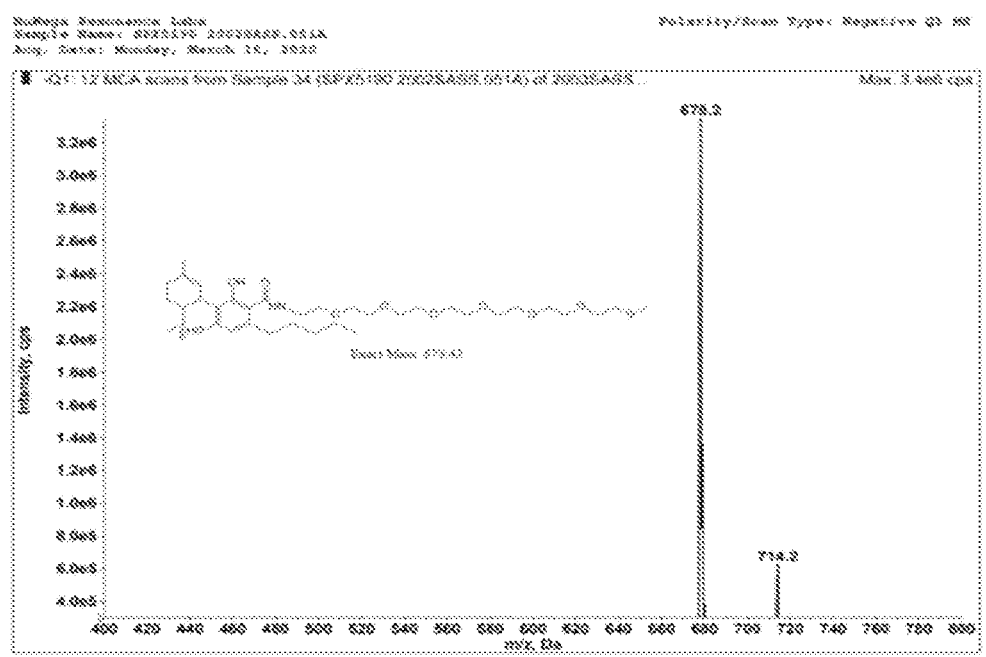
FIG. 3 is the mass spectrometry plot of cannabidiolic acid—m polyethylene glycol 7 adduct produced by another experiment described herein.
Figure 4:
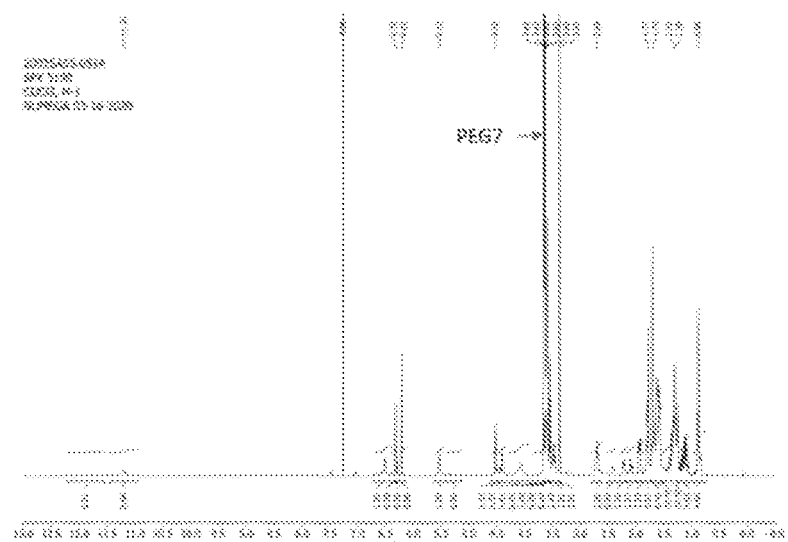
FIG. 4 is the NMR spectrum plot of cannabidiolic acid—m polyethylene glycol 7 adduct produced by the same experiment as in FIG. 3.

The presence of CBDA-mPEG7 is confirmed by mass spectrum as in FIG. 3. NMR of CBDA-mPEG7 is in FIG. 4.

Synthesis of CBDA-PEG7 through CBDA-NHS Ester Preparation

N-hydroxysuccinimide (NHS, 16 mg, 0.138 mmols) (reactant) was dissolved in 500 microliters of anhydrous N,N-Dimethylformamide (DMF) (solvent) and placed into 10 mL flame-dried vial equipped with magnetic stirring bar. To the NHS solution was added solid N,N'-dicyclohexylcarbodiimide (DCC, 33 mg, 0.160 mmols) (reactant). The reaction mixture was briefly stirred until all solid dissolved. Cannabidiolic acid (CBDA, 27 mg, 0.075 mmols) was then added to the NHS/DCC mixture and the reaction was stirred overnight at Room Temperature under nitrogen blanket to keep the reaction dry. Heavy precipitation of the reaction byproduct N,N'-dicyclohexylurea has occurred during the reaction. The white suspension was carefully transferred to 1.5 mL plastic Eppendorf tube. The reaction vial was washed with 500 µL DMF and the washings added to the plastic Eppendorf tube. The Eppendorf tube was centrifuged at 10,000 RPM for 10 minutes at 4° C. The clear supernatant was carefully transferred into a glass vial and solvent evaporated under high vacuum at 50° C. until dryness. The dry residue was purified by column chromatography on silica gel, eluting with a gradient of 5:1 to 7:3 Hexanes/Acetone. The pure CBDA-NHS product was isolated in 50% yield.

Reaction Scheme:

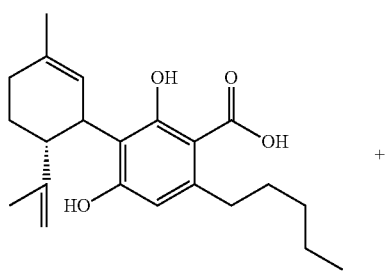

Exact Mass: 358.2
CBDA

+

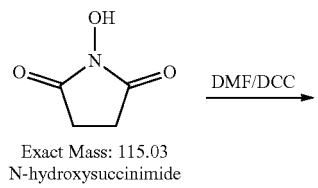

Exact Mass: 115.03
N-hydroxysuccinimide

DMF/DCC →

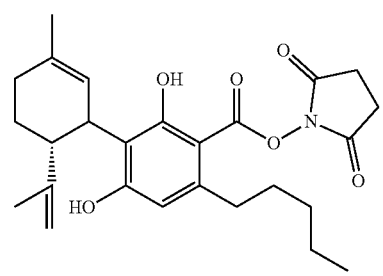

Exact Mass: 455.2
CBDA-NHS

CBDA-NHS active ester may then be used as an intermediary to generate mono-linked CBD-PEG7. CBDA-NHS ester may be reacted with mPEG7-amine in a dioxane solution buffered by pH 10 borate buffer. NHS is returned to its original state as N-Hydroxysuccinimide.

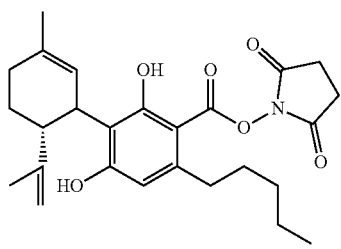

Exact Mass: 455.2
CBDA-NHS

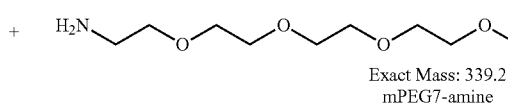

Exact Mass: 339.2
mPEG7-amine

Dioxane: Borate pH10

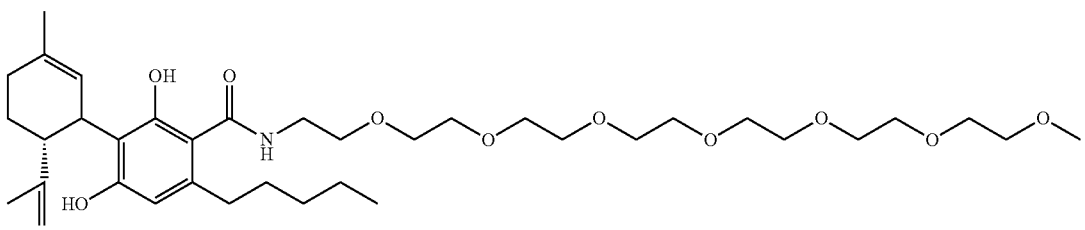

Exact Mass: 679.4
CBDA-mPEG7

Other Multi-Linked Cannabinoids

CBDA-NHS active ester may also be used as an intermediary to generate duo-linked CBD-PEG7, where one CBD is present at each end of the PEG7 chain. CBDA-NHS active ester is reacted with PEG7-diamine in a dioxane solution buffered by pH 10 borate buffer. NHS is returned to its original state as N-Hydroxysuccinimide.

2x 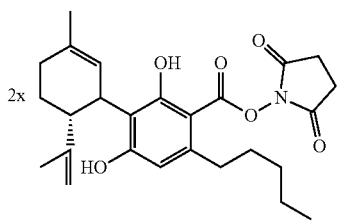

Exact Mass: 455.2
CBDA-NHS

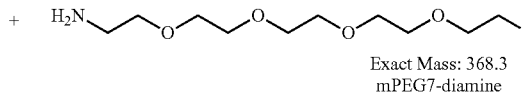

Exact Mass: 368.3
mPEG7-diamine

Dioxane: Borate pH10

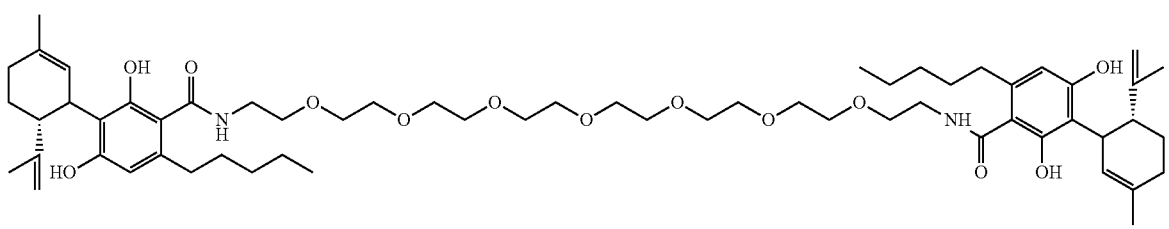

Exact Mass: 1048.7
Di-CBDA-mPEG7

Potential use of CBDA-NHS active ester extends to tri-linked CBDA, such that there are three CBDA-group attached to a tri-branch PEG7-amine:

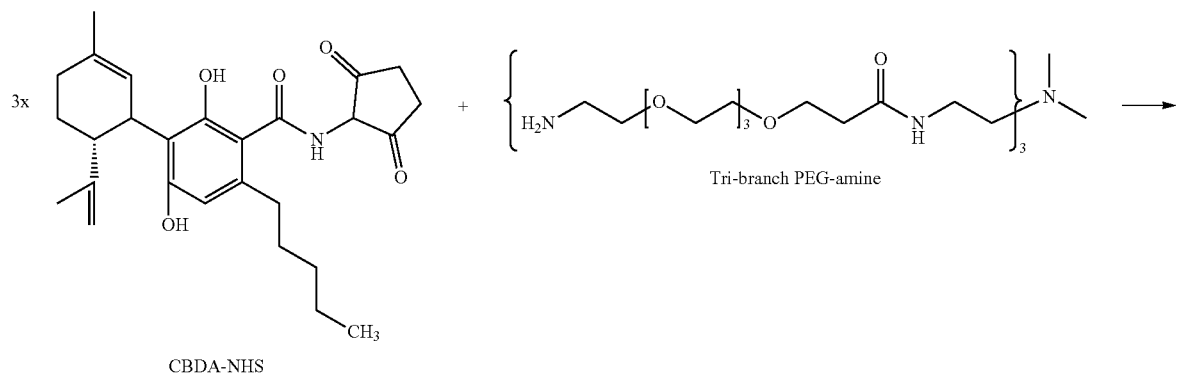

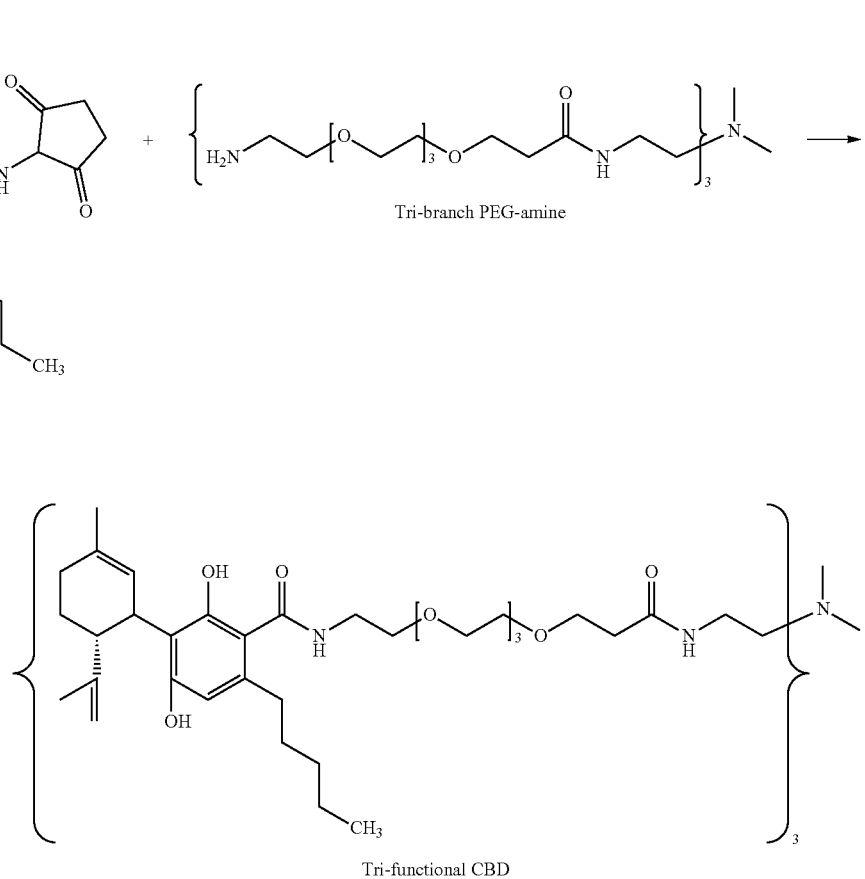

To produce a tri-branch PEG-amine ester, intermediary cannabinoid-NHS ester may be used. A tri-branch allows the presence of up to three different cannabinoids, thereby potentially allowing the administration of up to three different cannabinoids at precise dosages.

Synthesis of Cannabinoid Acid-PEG Ester through Hydroxy-PEG

Cannabinoid-acid-PEG ester prodrug may be synthesized to give more soluble cannabinoid prodrug, wherein cannabinoid-acid returns into its original molecular structure upon digestion by esterase. The carboxylic group on the phenolic ring of the cannabinoid-acid molecular structure is the site for esterification.

For example, CBDA prodrug may be synthesized for better a dissolution rate, in particular CBDA-PEG ester. Mono-linked CBDA-PEG may be synthesized using CBDA and hydroxy-PEG. The carboxylic group on CBDA reacts with the hydroxy group on hydroxy-PEG to give a CBDA-PEG ester prodrug, which has a higher solubility than CBDA. The CBDA-PEG ester prodrug returns to CBDA upon being released by in vivo esterase:

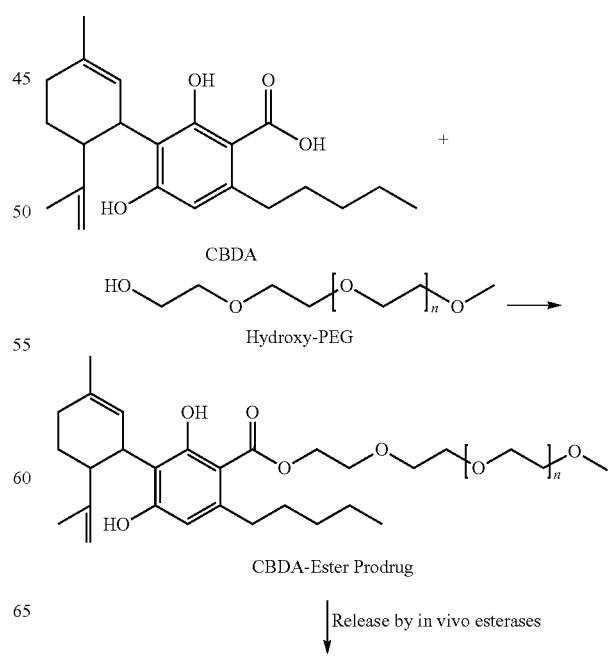

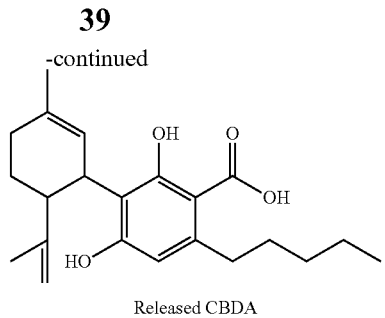

Released CBDA

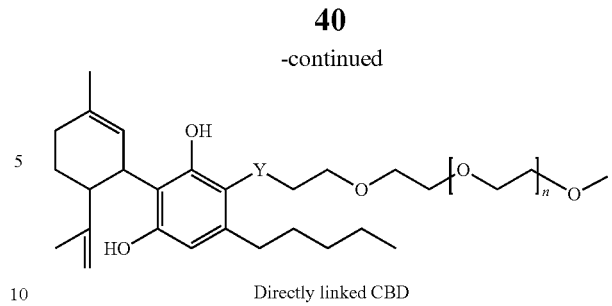

Directly linked CBD

In vivo esterase as present in human digestive system may work to release CBDA from the CBDA-PEG ester prodrugs, returning CBDA as to its original form. CBDA, upon entering the digestive tract, shall be digested and act in its original function.

Dual-linked or tri-linked cannabinoid-acid to hydroxy-PEG by esterification is also possible. Hydroxy-PEG with two or three hydroxy groups may serve as the basis for such linkage, resulting in a prodrug with one PEG molecule linked to two or three cannabinoid-acid at the hydroxy group by an esterification process. The two or three cannabinoid-acids may be the same or different. Upon exposure to esterase, the respective cannabinoid-acid is hydrolyzed and returns to its original state.

The example of CBDA-PEG ester above can be extended to other cannabinoid-acid having a carboxylic group on the phenolic ring, including cannabigerolic acid, tetrahydrocannabinolic acid, cannabinolic acid, cannabidivarinic acid, cannabichromenic acid, cannabivarinic acid, among other cannabinoid acids. By substituting CBDA with any other cannabinoid-acids in the above reactions, cannabinoid-acid-PEG ester may be produced.

Synthesis of Cannabinoid-PEG-Functional Group through Reactive PEG

Another pathway to link cannabinoid to PEG may be via halogenated cannabinoid. The carboxylic group on cannabinoid-acid molecules may be substituted by a halogen group, in particular fluoride (F), bromide (Br), or chloride (Cl).

Halogenated cannabinoids with a halogen group at the 2' carbon position on the phenolic ring in place of the carboxylic group are the starting material. Reactive PEG with various functional groups at either or both ends of the PEG-chain may react with the halogen group on the halogenated cannabinoid molecule. PEG-amine, PEG-hydroxide, or PEG-Sulfhydryl can be reacted with cannabinoid-halogen to arrive at cannabinoid-amine/hydroxy/sulfhydryl PEG.

In the example below, cannabidiol-halogen is the starting material and is reacted with reactive m-PEG with one functional group. Reaction scheme to create CBD-amine/hydroxy/sulfhydryl PEG:

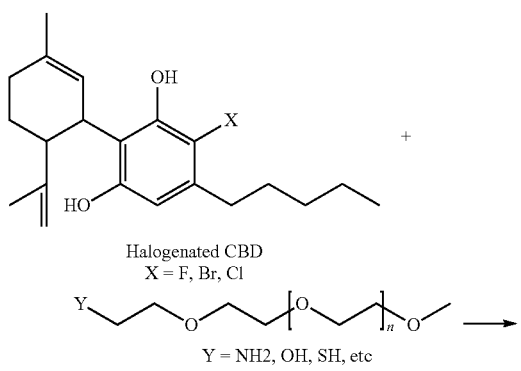

Similar reaction schemes may be implemented with other halogenated-cannabinoids having a phenolic ring, such as cannabigerol, tetrahydrocannabinol, cannabinol, cannabidivarin, cannabichromene, cannabivarin, among other cannabinoids. Reactive PEG molecules may also have more than one functional group.

Dual-linked or tri-linked cannabinoid-reactive PEG by is also possible. PEG with two or three functional groups may serve as the basis for such linkage, resulting in a prodrug with one PEG molecule linked to two or three cannabinoid at the 2' carbon position on the phenolic ring. The two or three cannabinoid-acids may be the same or different. The end result is a cannabinoid-PEG prodrug with high solubility, which releases cannabinoid once digested in vivo.

REFERENCES

Hruby, V, Girl, A K, Multivalent/Multifunctional Ligands with Agonist Activities at Opioid Receptors and Antagonist Activities At NK1 Receptor For Relief of Pain, WO2015/127451, World Intellectual Property Organization, 27 Jul. 2015.

Jacobsen, J R, Choi, S K, Combs, J, Fournier, E J, Klein, U., Pfeiffer J W, Thomas G R, Yu C., Moran E J. (2012). A multivalent approach to the discovery of long-acting β(2)-adrenoceptor agonists for the treatment of asthma and COPD. Bioorganic Med Chem Letter, 22(2):1213-8. DOI 10.1016/j.bmcl.2011.11.072.

Long, D D, Aggen, J B, Christensen, B G, Judice, J K, Hedge, S S, Kaniga, K, Krause, K M, Linsell, M S, Moran, E J, Pace, J L. (2008). A multivalent approach to drug discovery for Novel Antibiotic. The Journal of Antibiotics, 61, 595-602. https://doi.org/10.1038/ja.2008.79.

Zhou, L, Fengting, L, Liu, L, Wang, S. (2019). In Situ-Induced Multivalent Anticancer Drug Clusters in Cancer Cells for Enhancing Drug Efficacy. CCS Chem. 1, 97-105. DOI 0.31635/ccschem.019.20180015.

Variations and modifications will occur to those of skill in the art after reviewing this disclosure. The disclosed features may be implemented, in any combination and sub-combination (including multiple dependent combinations and sub-combinations), with one or more other features described herein. The various features described or illustrated above, including any components thereof, may be combined or integrated in other systems. Moreover, certain features may be omitted or not implements.

Examples of changes, substitutions, and alterations are ascertainable by one skilled in the art and could be made without departing from the scope of the information disclosed herein. All references cited are hereby incorporated by reference herein in their entireties and made part of this application.

What is claimed is:

1. A compound having the formula:

X—[CO—HN—(O—CH$_2$—CH$_2$)$_n$]—CH$_3$ wherein X is a cannabinoid having a phenolic group, and wherein X is linked to —[CO—HN—(O—CH$_2$—CH$_2$)$_n$]—CH$_3$ at the carbon at the 2' position on the phenolic ring.

2. The compound of claim 1, wherein n is 7 to give the formula:
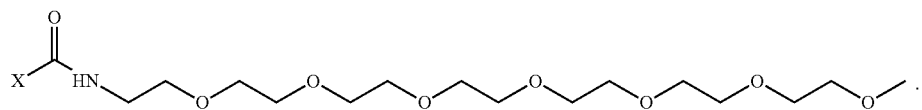
3. The compound of claim 1, wherein X is:
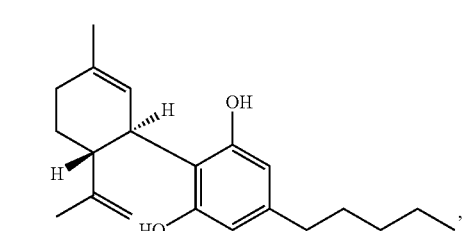,
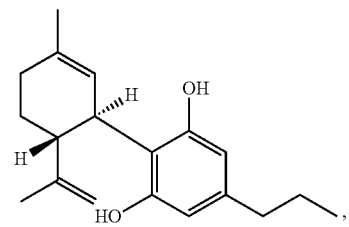,
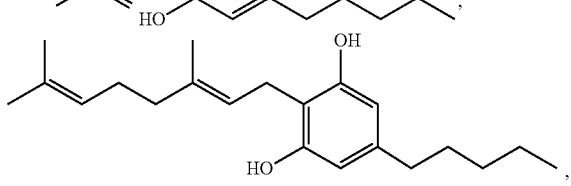,
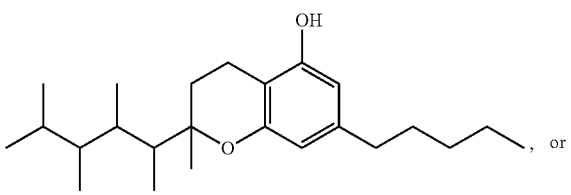,
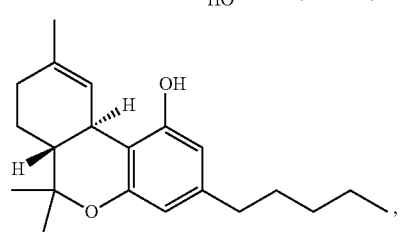,
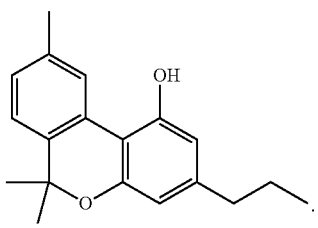, or
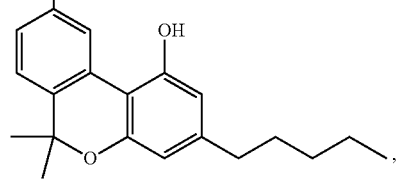.
* * * * *